(12) United States Patent
Ito

(10) Patent No.: US 9,265,882 B2
(45) Date of Patent: Feb. 23, 2016

(54) INDWELLING NEEDLE DEVICE

(75) Inventor: Toru Ito, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 0 days.

(21) Appl. No.: 14/123,906

(22) PCT Filed: Dec. 2, 2011

(86) PCT No.: PCT/JP2011/077935
§ 371 (c)(1),
(2), (4) Date: Dec. 4, 2013

(87) PCT Pub. No.: WO2012/169091
PCT Pub. Date: Dec. 13, 2012

(65) Prior Publication Data
US 2014/0100529 A1   Apr. 10, 2014

(30) Foreign Application Priority Data

Jun. 7, 2011 (JP) .................................. 2011-127538

(51) Int. Cl.
*A61M 25/06* (2006.01)
*A61M 5/158* (2006.01)

(52) U.S. Cl.
CPC ........... *A61M 5/158* (2013.01); *A61M 25/0606* (2013.01); *A61M 25/0631* (2013.01); *A61M 25/0637* (2013.01); *A61M 2005/1587* (2013.01)

(58) Field of Classification Search
CPC ................. A61M 25/0618; A61M 2005/3201; A61M 5/3297; A61M 2025/0175; A61M 5/3293; A61M 25/0631; A61M 25/0637; A61M 25/0097; A61M 5/158; A61M 25/0606
See application file for complete search history.

(56) References Cited

U.S. PATENT DOCUMENTS

| 4,834,718 A | 5/1989 | McDonald |
| 5,000,740 A | 3/1991 | Ducharme et al. |
| 5,108,376 A * | 4/1992 | Bonaldo ...................... 604/171 |

(Continued)

FOREIGN PATENT DOCUMENTS

| JP | 3-063066 | 3/1991 |
| JP | 2002-210018 | 7/2002 |

(Continued)

OTHER PUBLICATIONS

Extended European Search Report issued for corresponding European Application No. 11867479.5, dated Feb. 25, 2015.
Extended European Search Report issued in corresponding European Application No. 13748561.1, Sep. 18, 2015, 9 pages.

*Primary Examiner* — Bhisma Mehta
*Assistant Examiner* — James Ponton
(74) *Attorney, Agent, or Firm* — Hamre, Schumann, Mueller & Larson, P.C.

(57) ABSTRACT

A hub can be displaced between an initial position at which the hub is located on a front end side of an inner cavity of a shield and an inner needle penetrates an outer needle and a retracted position at which the hub is located on a rear end side of the inner cavity of the shield and the inner needle is housed within the inner cavity of the shield. A stopper includes an insertion portion that is inserted into the inner cavity of the shield and a base portion that is located on a rear end of the insertion portion. The base portion includes a roof portion that exposes part of an outer circumferential face of a tube connected to the hub and covers the remainder thereof, and a pair of grasping portions that are arranged to sandwich the tube and can be elastically displaced so as to grip the tube.

8 Claims, 25 Drawing Sheets

(56) References Cited

U.S. PATENT DOCUMENTS

| | | | |
|---|---|---|---|
| 5,690,617 A * | 11/1997 | Wright | 604/179 |
| 5,743,882 A | 4/1998 | Luther | |
| 6,616,631 B2 | 9/2003 | Takagi et al. | |
| 6,969,376 B2 | 11/2005 | Takagi et al. | |
| 2003/0176842 A1 | 9/2003 | Wilkinson et al. | |
| 2007/0142785 A1* | 6/2007 | Lundgaard et al. | 604/179 |
| 2009/0018511 A1 | 1/2009 | Fujii et al. | |
| 2012/0220943 A1 | 8/2012 | Ito et al. | |
| 2013/0066276 A1 | 3/2013 | Ito et al. | |
| 2015/0011942 A1 | 1/2015 | Ito et al. | |

FOREIGN PATENT DOCUMENTS

| | | |
|---|---|---|
| JP | 2003/265610 | 9/2003 |
| JP | 2009-254576 | 11/2009 |
| JP | 4506834 | 7/2010 |
| JP | 2011-120829 | 6/2011 |
| JP | 2011-120830 | 6/2011 |
| JP | 2011-251081 | 12/2011 |
| JP | 2013-022069 | 2/2013 |
| WO | WO 2007/083770 | 7/2007 |
| WO | 2012/169091 | 12/2012 |

* cited by examiner

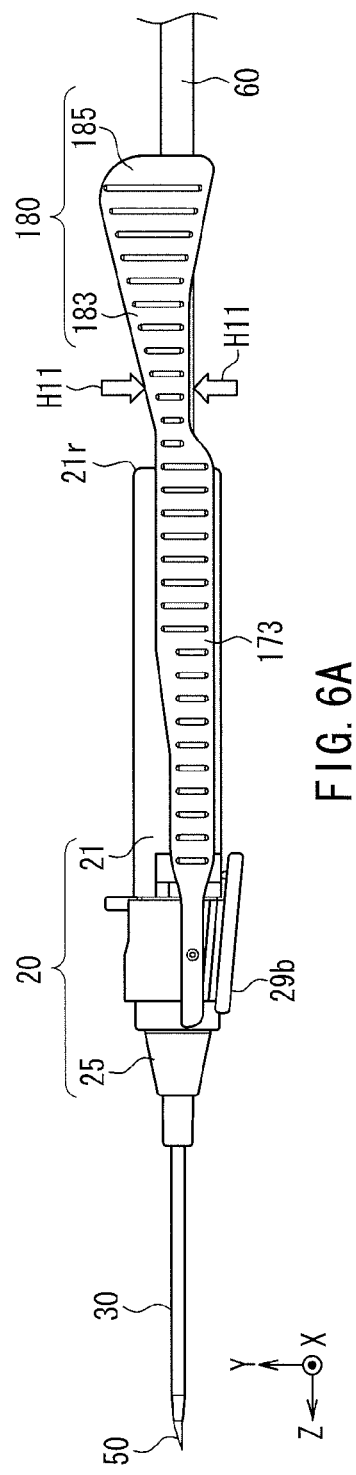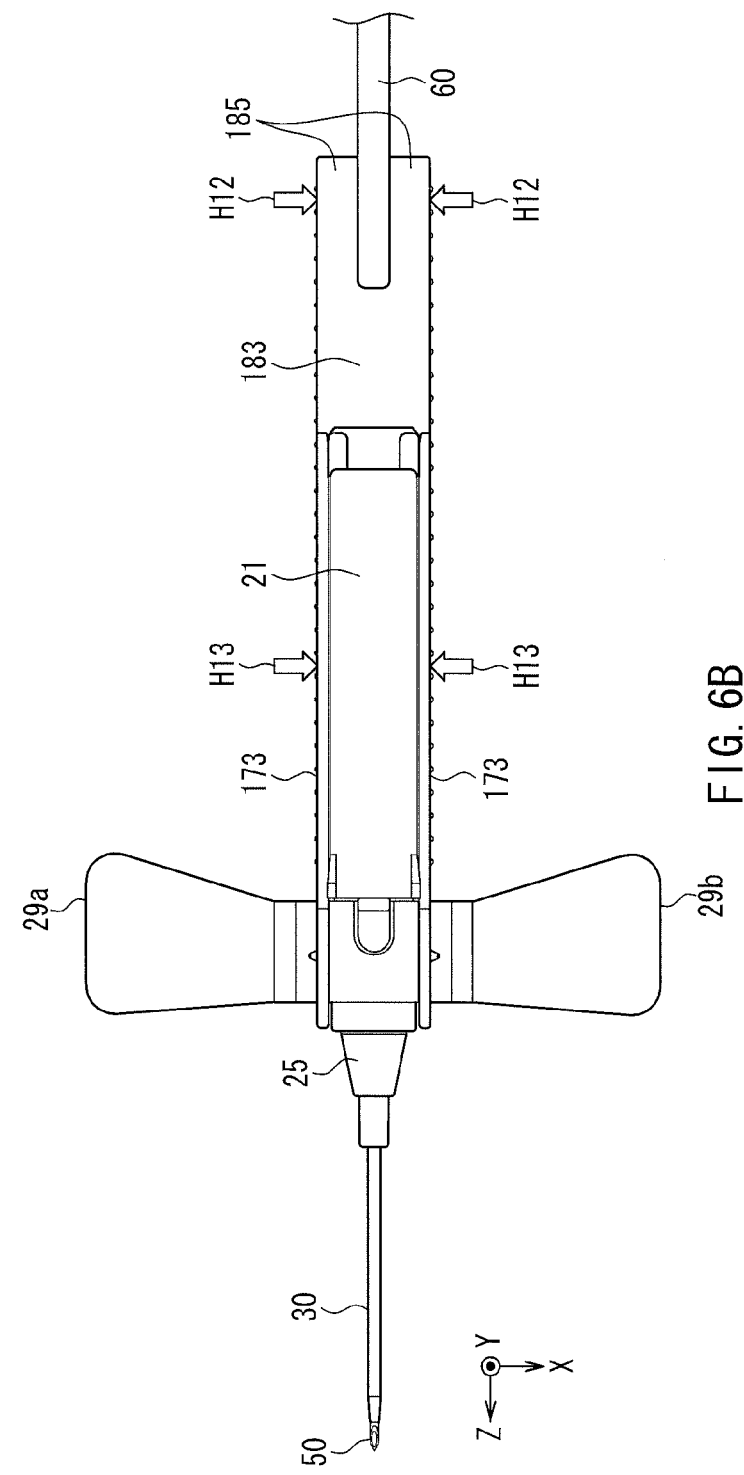
FIG. 6A
FIG. 6B

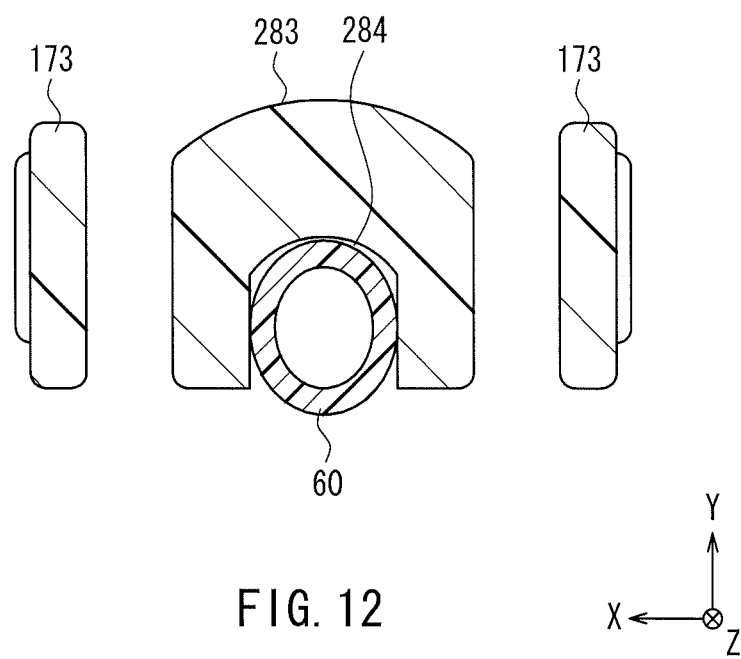
F I G. 12

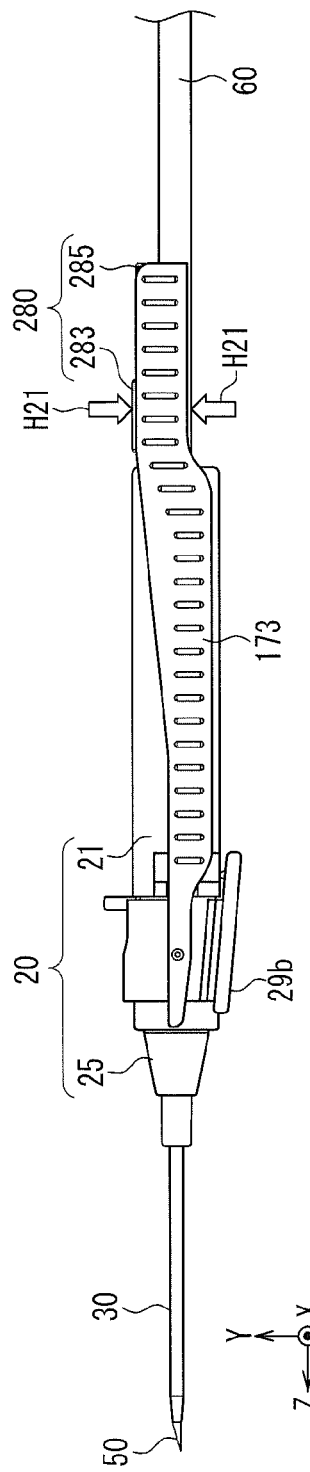
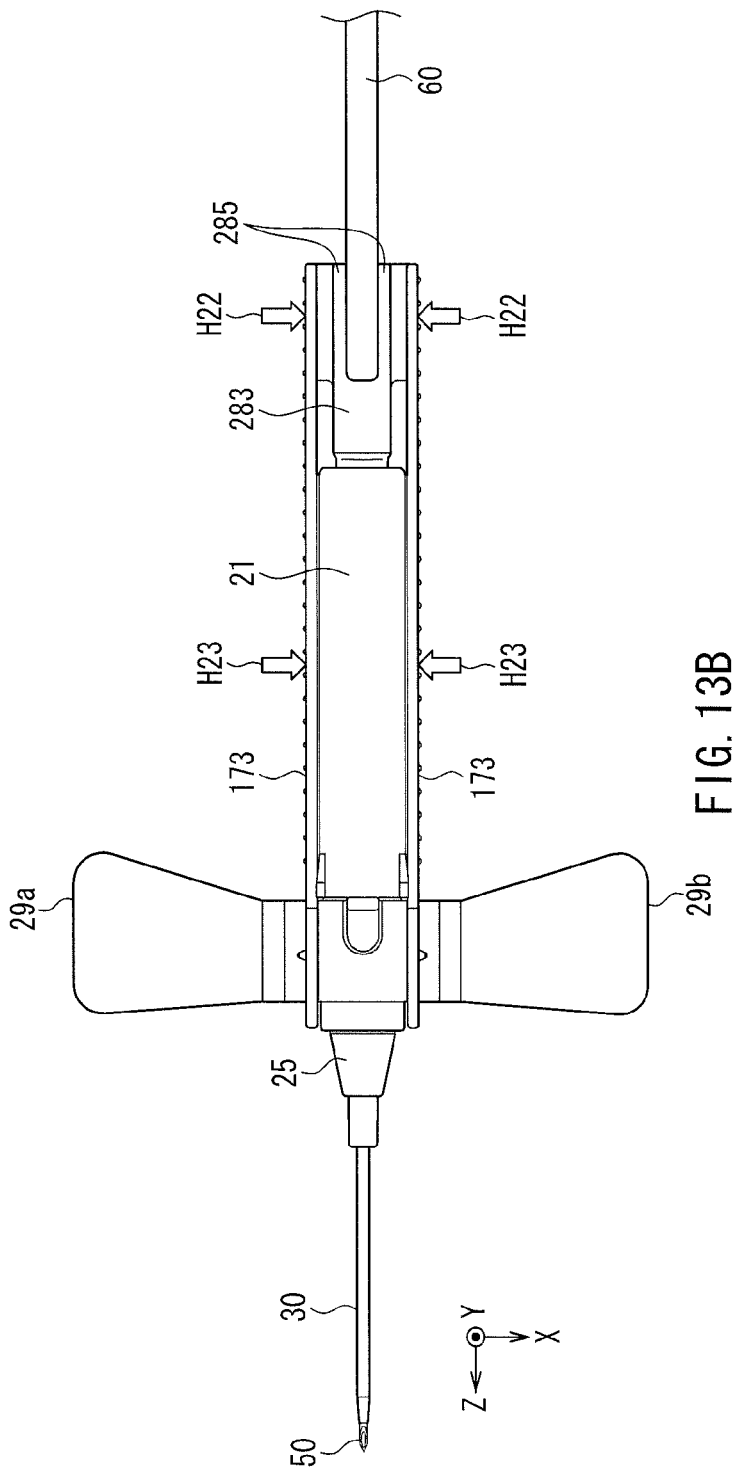
FIG. 13A
FIG. 13B

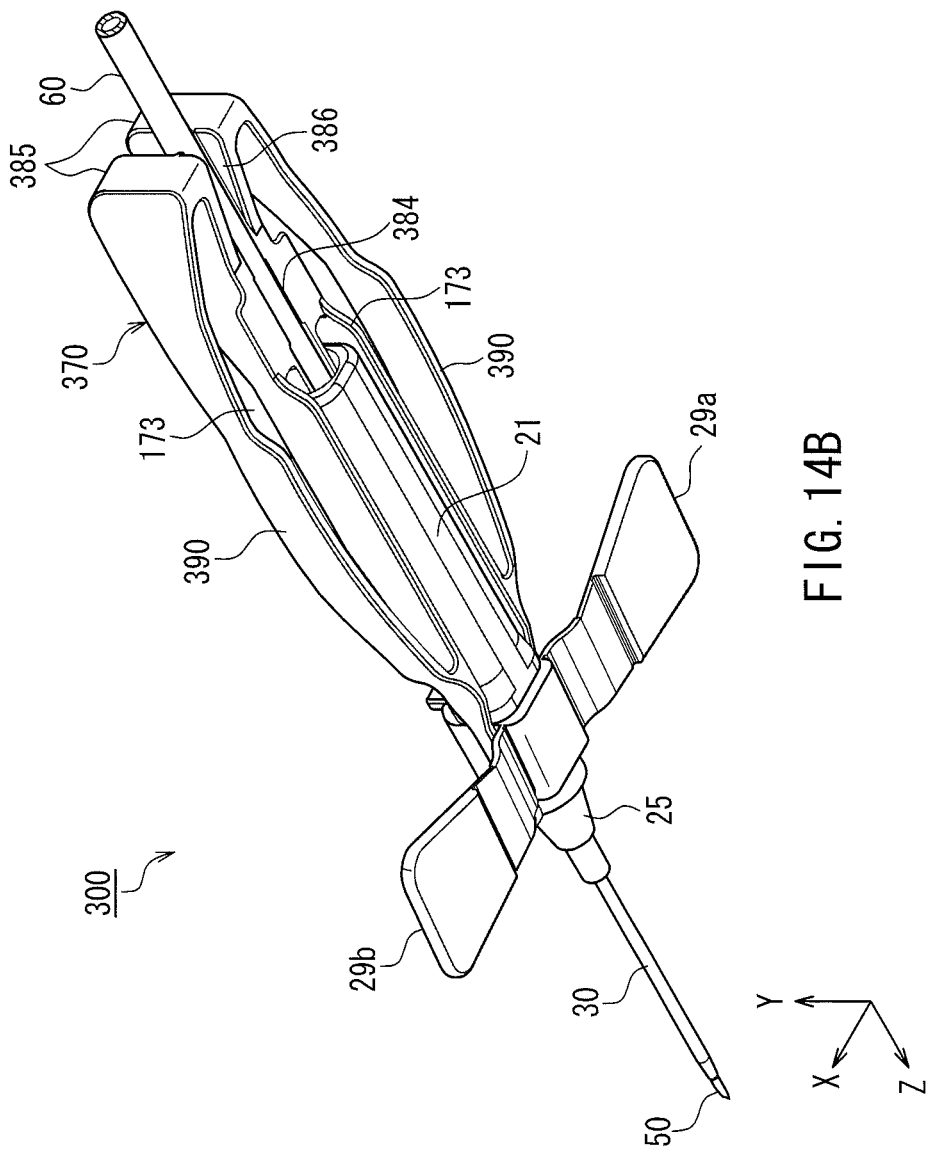
F I G. 14B

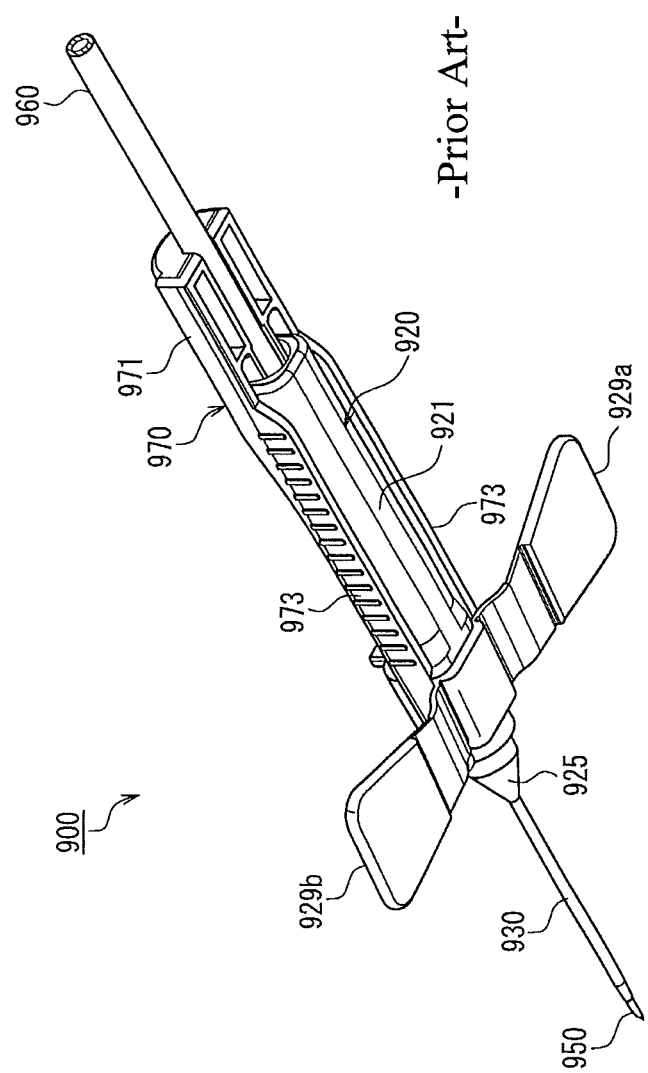
FIG. 18B -Prior Art-

-Prior Art-

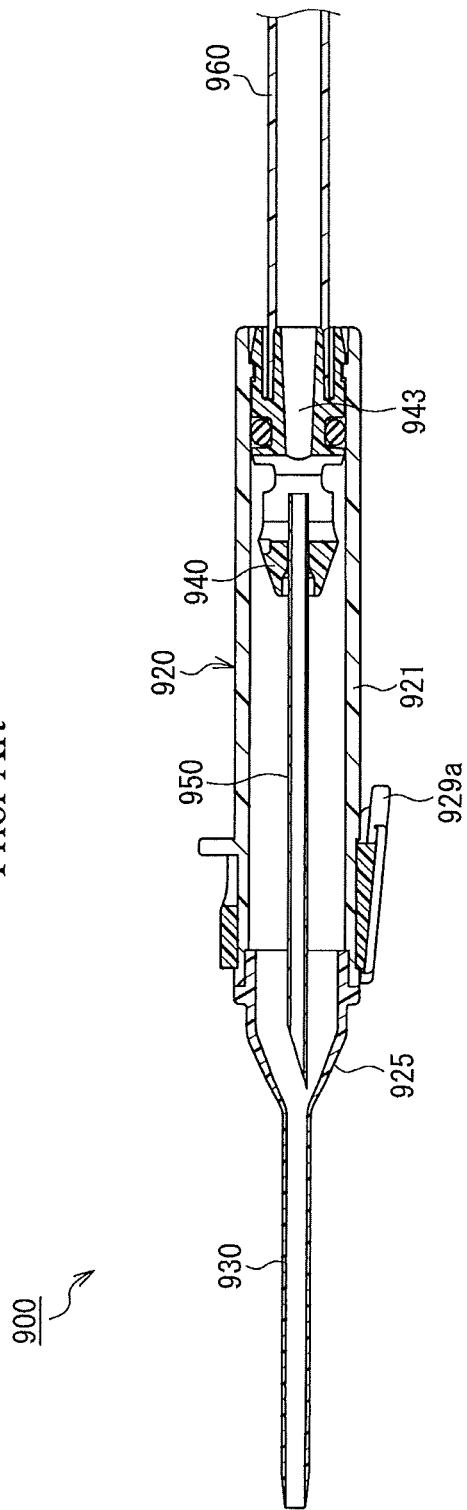
FIG. 21 -Prior Art-

INDWELLING NEEDLE DEVICE

TECHNICAL FIELD

The present invention relates to an indwelling needle device that includes a soft outer needle and a hard inner needle, and that is configured such that it can be inserted into a patient in a state in which a leading end of the inner needle protrudes from a leading end of the outer needle and then the inner needle can be retracted from the outer needle.

BACKGROUND ART

Indwelling needle devices are widely used for such treatments as infusion, blood transfusion, and extracorporeal blood circulation. In such treatments, leaving a metal needle inside a blood vessel may injure the blood vessel. Thus, indwelling needle devices are known that include a soft outer needle and a hard inner needle. The outer needle and the inner needle are inserted into a blood vessel of a patient in a state in which a leading end of the inner needle protrudes from a leading end of the outer needle, and then the inner needle is retracted from the outer needle, so that only the outer needle is left inside the patient. The possibility of the extant soft outer needle injuring the blood vessel of the patient is low.

FIG. 18A is a perspective view of an example of such a conventional indwelling needle device 900 (see Patent Document 1, for example) as seen from above. FIG. 18B is a perspective view thereof as seen from below. FIG. 19 is a cross-sectional view of the conventional indwelling needle device 900 taken along a vertical plane containing line 19-19 in FIG. 18A and seen in the direction of arrows 19. For the sake of convenience of description, a side that is inserted into the patient (the left side in FIGS. 18A, 18B, and 19) is referred to as a "front side", and a side that is opposite from this side is referred to as a "rear side".

The indwelling needle device 900 includes a shield 920 configured by a shield tube 921 that has an approximately cylindrical shape, and an outer hub 925 that is fixed to an end (front end) of the shield tube 921. A soft outer needle 930 is fixed to a front end of the outer hub 925.

A pair of wings 929a and 929b are provided on an outer circumferential face of the shield tube 921 in the vicinity of its outer hub 925 side end. The wings 929a and 929b are flexible, and can be swung up and down.

A hub 940 is inserted in an inner cavity of the shield 920 so as to be movable in a longitudinal direction (i.e., front-rear direction) of the shield 920. A hard inner needle 950 made of metal is fixed to a front end of the hub 940, and one end of a flexible tube 960 is connected to a rear end of the hub 940. The inner needle 950 and the tube 960 are in communication with each other via a longitudinal penetration path 943 that penetrates the hub 940 in the front-rear direction.

In FIGS. 18A, 18B, and 19, the hub 940 is located on the front end side of the inner cavity of the shield 920. This position of the hub 940 relative to the shield 920 is referred to as an "initial position". At the initial position, the inner needle 950 held by the hub 940 penetrates the outer needle 930, and the leading end of the inner needle 950 protrudes to the outside from the leading end of the outer needle 930.

In order to maintain the hub 940 at the initial position, a stopper 970 is used. FIG. 20 is a perspective view of the stopper 970. An approximately semi-cylindrical insertion portion 972 and a pair of fixing portions 973 extend from an approximately semi-cylindrical base end portion 971. The insertion portion 972 is disposed between the pair of fixing portions 973, and these portions are parallel to one another.

As shown in FIG. 19, the insertion portion 972 of the stopper 970 is inserted from the rear end of the shield tube 921. When a leading end of the insertion portion 972 hits the rear end of the hub 940 and pushes the hub 940 toward the front side, the hub 940 can be disposed at the initial position. As shown in FIG. 18B, the tube 960 is partially exposed on the lower face side of the base end portion 971 of the stopper 970.

The inner needle 950 and the outer needle 930 are inserted into a blood vessel of the patient in a state in which the hub 940 is kept at the initial position. In order to maintain the hub 940 at the initial position during puncture, the stopper 970 has to be prevented from being displaced relative to the shield 920. Accordingly, an operator may grip with two fingers the base end portion 971 of the stopper 970 in the vertical direction (see arrows H91 in FIG. 18A) or in the horizontal direction (see arrows H92 in FIG. 18A), or may grip the pair of fixing portions 973 in the horizontal direction (see arrows H93 in FIG. 18A). Alternatively, the operator may bend the pair of wings 929a and 929b upward such that the pair of fixing portions 973 are sandwiched and fixed between the pair of wings 929a and 929b and the shield tube 921, and grip with two fingers the pair of wings 929a and 929b overlapping each other.

Subsequently, the stopper 970 is pulled out of the shield 920, and then the tube 960 is pulled from the shield 920. Accordingly, the hub 940 and the inner needle 950 are moved together with the tube 960 toward the rear side relative to the shield 920, and the inner needle 950 is housed within the shield 920 as shown in FIG. 21. The position of the hub 940 relative to the shield 920 shown in FIG. 21 is referred to as a "retracted position". In this state, the indwelling needle device 910 is fixed to the patient using adhesive tape or the like. Only the soft outer needle 930 is left inside the patient in a state in which it is inserted in the patient.

Patent Document 1: Japanese Patent No. 4506834

DISCLOSURE OF INVENTION

Problem to be Solved by the Invention

As described above, according to the conventional indwelling needle device 900, it is necessary to perform an operation that pulls the tube 960 relative to the shield 920 in order to house the inner needle 950 within the shield 920 as shown in FIG. 21. Before or simultaneously with this operation, the stopper 970 has to be pulled out of (removed from) the shield 920. The function of the stopper 970 is only to maintain the hub 940 at the initial position during puncture, and the inner needle 950 cannot be retracted merely by pulling out the stopper 970.

However, when only the stopper 970 has been pulled out of the shield 920, the operator may mistakenly think that the inner needle 950 has been housed within the shield 920, resulting in an operational error in which the operator forgets to pull the tube 960. As a result, the inner needle 950 is left inside the patient in a state in which it protrudes from the leading end of the outer needle 930, and, thus, the leading end of the hard inner needle 950 may injure the blood vessel of the patient.

The method for gripping the indwelling needle device 900 during puncture is different from operator to operator, but some gripping methods require changing the grip position after the puncture in order to pull the tube 960, which makes the operation complicated.

It is a first object of the present invention to reduce the possibility that an operational error will occur in which the operator pulls out only the stopper after the puncture and forgets to house the inner needle within the shield. Furthermore, it is a second object of the present invention to reduce the need for changing the grip position between when performing puncture and when housing the inner needle within the shield.

Means for Solving Problem

The present invention is directed to an indwelling needle device, including: a shield that has an inner cavity; a soft outer needle that is fixed to a front end of the shield; a hub that is disposed within the inner cavity of the shield and is movable in a longitudinal direction of the shield; a hard inner needle that is fixed to a front end of the hub; a tube that is connected to a rear end of the hub; and a stopper that can be inserted into and pulled out of the inner cavity of the shield from a rear end of the shield. The hub can be displaced between an initial position at which the hub is located on a front end side of the inner cavity of the shield and the inner needle penetrates the outer needle and protrudes from a leading end of the outer needle, and a retracted position at which the hub is located on a rear end side of the inner cavity of the shield and the inner needle is housed within the inner cavity of the shield. The stopper includes an insertion portion that is inserted into the inner cavity of the shield and a base portion that is located on a rear end of the insertion portion. When the insertion portion is inserted into the inner cavity of the shield and a leading end thereof is caused to abut against the hub located at the initial position, the base portion is located outside the shield. The base portion includes a roof portion that exposes part of an outer circumferential face of the tube and covers the remainder thereof, and a pair of grasping portions that are arranged to sandwich the tube and can be elastically displaced so as to grip the tube.

Effects of the Invention

According to the present invention, the base portion includes the roof portion and the pair of grasping portions, and, thus, after the puncture with the indwelling needle device, the tube can be pulled together with the stopper by gripping the base portion and pulling the stopper out of the shield. Accordingly, the possibility of an operational error in which the operator pulls out only the stopper and forgets to house the inner needle within the shield can be reduced.

Furthermore, when puncture with the indwelling needle device has been performed in a state in which the base portion is gripped, the inner needle can be housed within the shield after the puncture, without changing the grip position. Accordingly, a series of operations when using the indwelling needle device can be performed quickly and efficiently.

BRIEF DESCRIPTION OF DRAWINGS

FIGS. 6A and 6B are views showing typical grip positions when inserting the indwelling needle device according to Embodiment 1 of the present invention, wherein FIG. 6A is a side view thereof, and FIG. 6B is a plan view thereof.

FIG. 12 is a cross-sectional view of the indwelling needle device according to Embodiment 2 of the present invention taken along a vertical plane containing line 12-12 in FIG. 9A and seen in the direction of arrows 12.

FIGS. 13A and 13B are views showing typical grip positions when inserting the indwelling needle device according to Embodiment 2 of the present invention, wherein FIG. 13A is a side view thereof, and FIG. 13B is a plan view thereof.

FIG. 14B is a perspective view of the indwelling needle device according to Embodiment 3 of the present invention as seen from below.

FIGS. 17A and 17B are views showing typical grip positions when inserting the indwelling needle device according to Embodiment 3 of the present invention, wherein FIG. 17A is a side view thereof, and FIG. 17B is a plan view thereof.

FIG. 18B is a perspective view of the conventional indwelling needle device as seen from below.

FIG. 21 is a cross-sectional view of the conventional indwelling needle device shown in FIGS. 18A and 18B taken along the same plane as in FIG. 19, with an inner needle being housed within a shield.

DESCRIPTION OF THE INVENTION

Figure 1A:
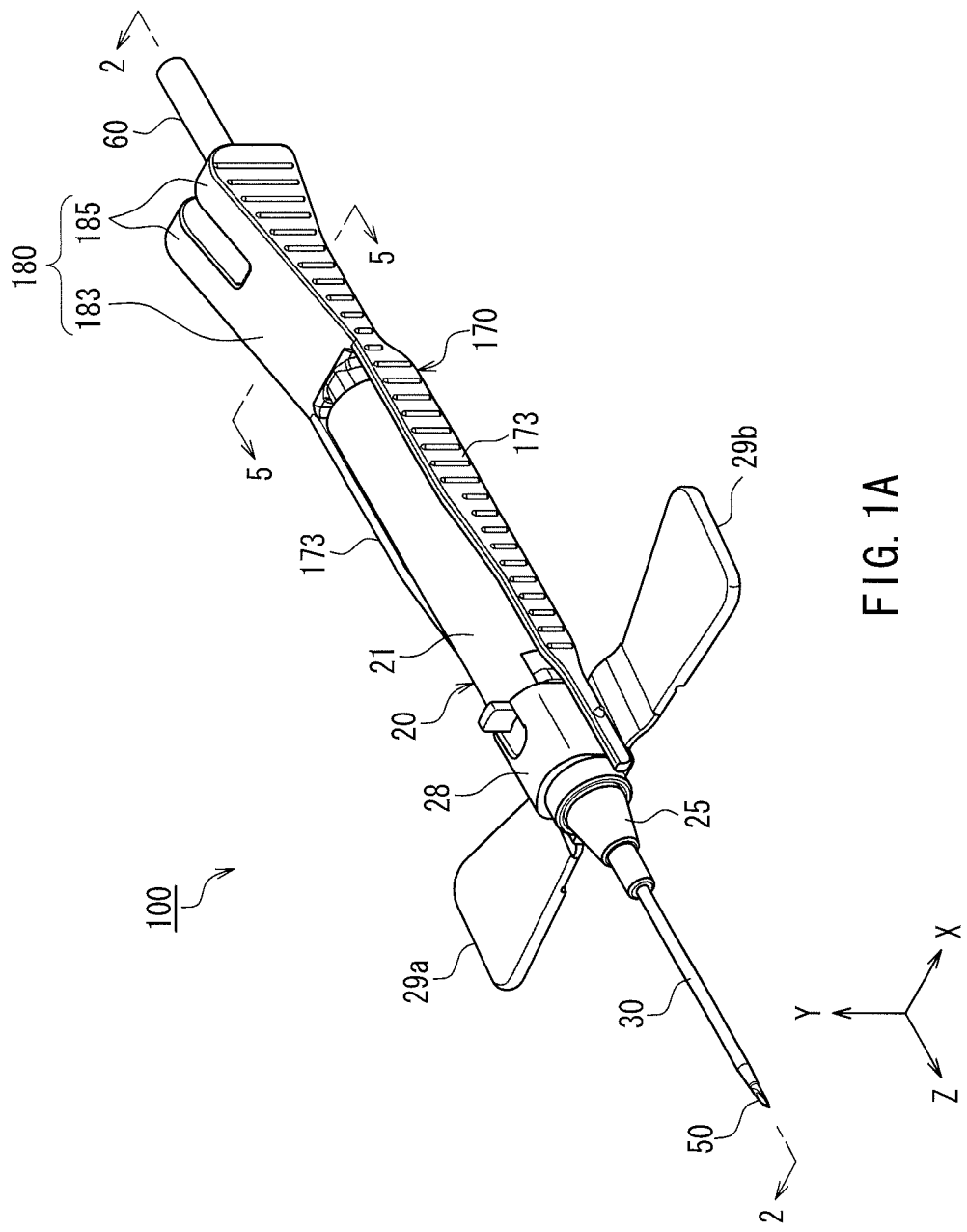
FIG. 1A is a perspective view of an indwelling needle device according to Embodiment 1 of the present invention as seen from above.

In the indwelling needle device of the present invention, it is preferable that a dimension of the pair of grasping portions in a direction orthogonal to a direction in which the pair of grasping portions sandwich the tube and to a longitudinal direction of the insertion portion is larger than that of the roof portion. Accordingly, the indwelling needle device and the stopper can be gripped stably with the pair of grasping portions.

Furthermore, it is preferable that the roof portion and the pair of grasping portions are arranged in that order from an insertion portion side. Accordingly, the pair of grasping portions can be arranged at the rear end of the stopper, which is advantageous for elastically displacing the pair of grasping portions.

In this configuration, it is preferable that an upper face of the roof portion is inclined such that a height in a direction orthogonal to a direction in which the pair of grasping portions sandwich the tube and to a longitudinal direction of the insertion portion is lower toward the insertion portion. Moreover, it is preferable that the upper faces of the pair of grasping portions are inclined as well. Accordingly, when puncture with the indwelling needle device has been performed in a state in which the pair of grasping portions are gripped, the stopper easily can be pulled out of the shield after the puncture.

Furthermore, it is preferable that the roof portion causes part of the outer circumferential face of the tube to protrude from the roof portion. Accordingly, when the roof portion is gripped in the vertical direction, the tube can be gripped reliably together with the roof portion. Thus, the inner needle can be housed reliably within the shield simultaneously with pulling the stopper out of the shield.

Furthermore, it is preferable that a groove to which the tube is fitted is formed in the roof portion. Accordingly, the tube can be held stably in the roof portion.

Furthermore, it is preferable that the roof portion causes part of the outer circumferential face of the tube to be exposed in a direction orthogonal to a direction in which the pair of grasping portions sandwich the tube and to a longitudinal direction of the insertion portion. Accordingly, when the base portion is gripped in the vertical direction, the tube can be gripped together with the base portion.

Furthermore, it is preferable that the stopper further includes a pair of fixing portions that are arranged to sandwich the insertion portion. In this case, it is preferable that, when the pair of grasping portions are elastically displaced so as to grip the tube, the pair of fixing portions are displaced in orientations in which the fixing portions move away from the insertion portion. Accordingly, interference can be avoided between the fixing portions and the shield by gripping the pair of grasping portions, when inserting the insertion portion into the shield and when pulling the stopper out of the shield.

Furthermore, the indwelling needle device may be configured such that the stopper further includes a pair of fixing portions that are arranged to sandwich the insertion portion and a pair of bridging portions that link the pair of grasping portions and the pair of fixing portions. In this case, it is preferable that, when the pair of bridging portions are elastically displaced so as to approach each other, the pair of grasping portions are displaced so as to grip the tube. Accordingly, the number of types of gripping methods that can perform puncture and then house the inner needle without changing the grip position increases. In this configuration, when the pair of bridging portions are elastically displaced so as to approach each other, the pair of fixing portions further may be displaced in orientations in which the fixing portions move away from the insertion portion. Accordingly, interference can be avoided between the fixing portions and the shield by gripping the pair of bridging portions, when inserting the insertion portion into the shield and when pulling the stopper out of the shield.

Hereinafter, the present invention will be described in detail while showing preferred embodiments thereof. However, it goes without saying that the present invention is not limited to the embodiments below. In the drawings that will be referred to in the following description, only main members of constituent members of the embodiments of the present invention that are necessary for the description of the present invention are shown in a simplified manner for the sake of convenience of description. Accordingly, the present invention may include optional constituent members that are not shown in the drawings below. Moreover, it should be understood that the dimensions of the members in the drawings below are not faithful representation of the dimensions of actual constituent members, dimensional ratios of those members, and the like.

Embodiment 1

Figure 1B:
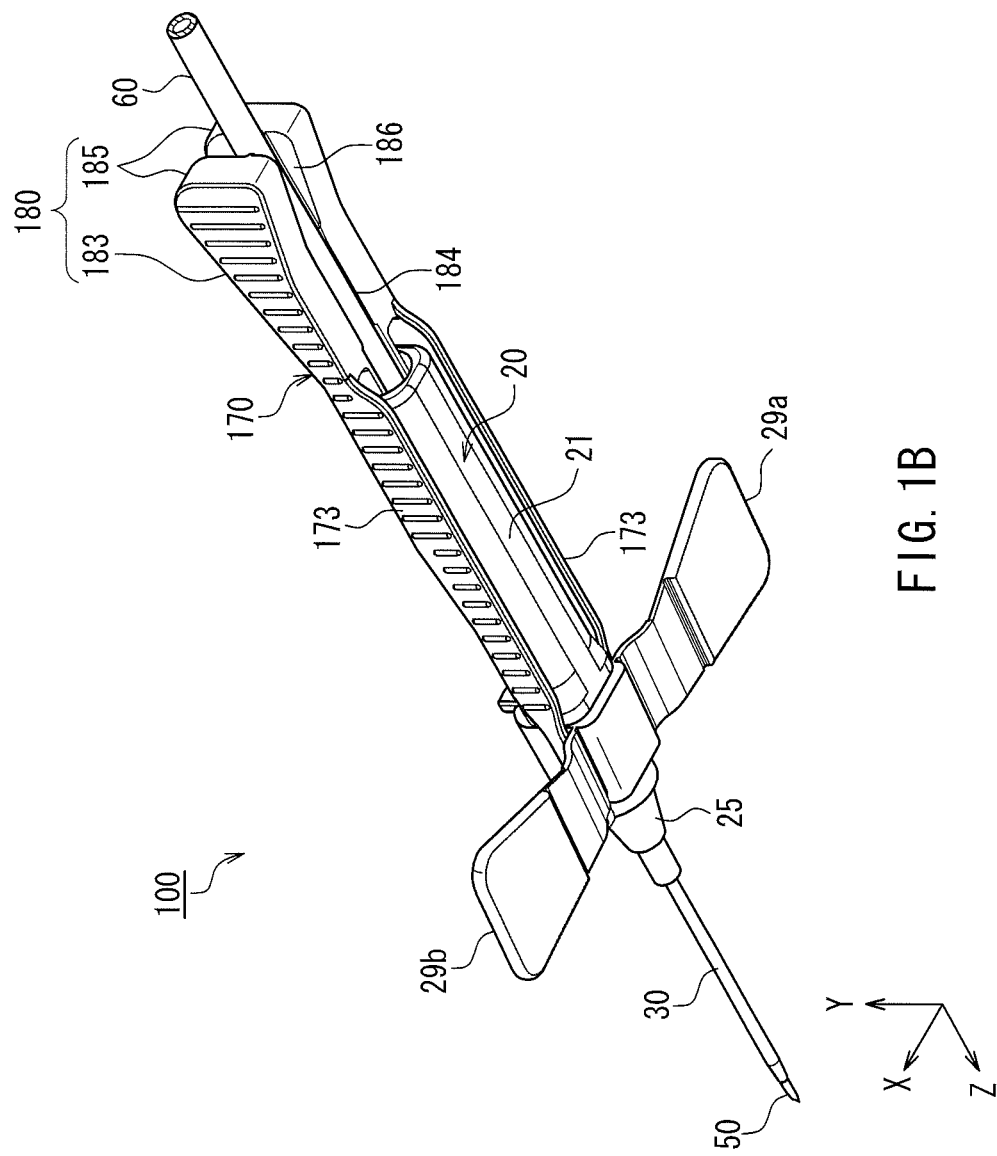
FIG. 1B is a perspective view of the indwelling needle device according to Embodiment 1 of the present invention as seen from below.
Figure 2:
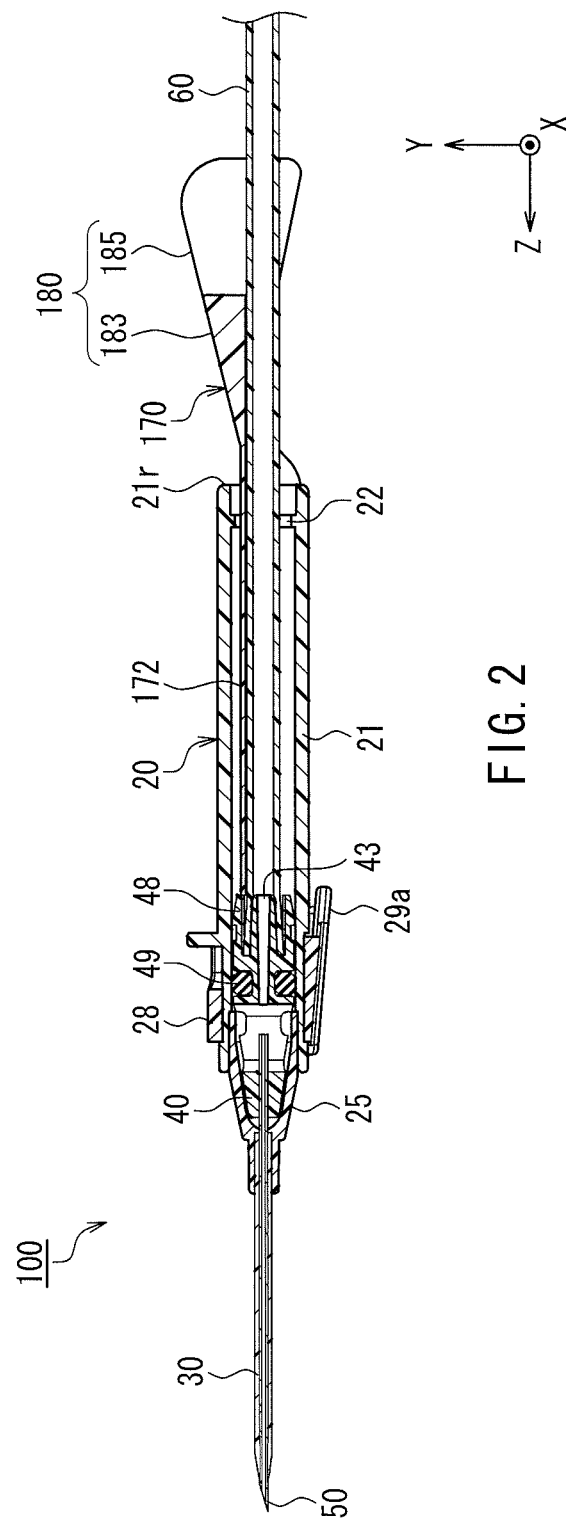
FIG. 2 is a cross-sectional view of the indwelling needle device according to Embodiment 1 of the present invention taken along a vertical plane containing line 2-2 in FIG. 1A and seen in the direction of arrows 2.

FIG. 1A is a perspective view, as seen from above, of an indwelling needle device 100 according to Embodiment 1 of the present invention with a hub being at the initial position, and FIG. 1B is a perspective view thereof as seen from below. For the sake of convenience of description, an orthogonal coordinate system is set in which the longitudinal direction of the indwelling needle device 100 is taken as a Z axis, and the horizontal axis and the vertical axis orthogonal to the Z axis are respectively taken as an X axis and a Y axis. Furthermore, a side in the direction of the Y axis arrow (i.e., the upper side in FIGS. 1A and 1B) is referred to as an "upper side", and a side that is opposite from this side is referred to as a "lower side". Note that the "horizontal direction" and the "vertical direction" do not refer to the actual orientations when using the indwelling needle device 100. Moreover, a side that is inserted into the patient (a side in the direction of the Z axis arrow, that is, the left side in FIGS. 1A and 1B) is referred to as a "front side", and a side that is opposite from this side is referred to as a "rear side". FIG. 2 is a cross-sectional view of the indwelling needle device 100 taken along a vertical plane (YZ plane) containing line 2-2 in FIG. 1A and seen in the direction of arrows 2.

The indwelling needle device 100 includes a shield 20. The shield 20 has a shield tube 21 and an outer hub 25 that is fixed to an end (front end) of the shield tube 21. The shield tube 21 has an approximately cylindrical shape having a constant inner diameter. An engagement protrusion 22 that is continuous in a circumferential direction is formed in an inner circumferential face of the shield tube 21 in the vicinity of an end (rear end) that is opposite from the outer hub 25. The outer hub 25 is approximately funnel-shaped, and a soft outer needle 30 is fixed to an end (front end) thereof that is opposite from the shield tube 21. The outer needle 30 has an approximately cylindrical shape. Although there is no particular limitation on the materials for the shield tube 21 and the outer hub 25, a hard material is preferable, and, for example, polycarbonate, polypropylene, and the like can be used. Preferably, the shield tube 21 and the outer hub 25 have transparency or translucency, so that blood and a hub 40 inside their respective inner cavities can be seen therethrough. Although there is no particular limitation on the material for the outer needle 30, a soft material is preferable, and, for example, polypropylene, polyurethane elastomer, fluororesin such as polytetrafluoroethylene, and the like can be used. Preferably, the outer needle 30 has transparency or translucency, so that blood and an inner needle 50 inside its inner cavity can be seen therethrough. It should be noted that the outer hub 25 and the outer needle 30 also may be formed integrally using the soft material described above.

Reference numerals 29a and 29b indicate wings that extend approximately parallel to the X axis. The wings 29a and 29b are provided on a fixing member 28 having an approximately cylindrical shape. The wings 29a and 29b are installed on the shield 20 by externally fitting the fixing member 28 to the outer circumferential face of the shield tube 21 in the vicinity of its outer hub 25 side end. Although there is no particular limitation on the material for the wings 29a and 29b, a soft material is preferable, and, for example, polypropylene, vinyl chloride, polyethylene, olefin or polystyrene thermoplastic elastomer, and the like can be used. It should be noted that the wings 29a and 29b also may be integrally molded with the shield 20.

The hub 40 is inserted in the inner cavity of the shield 20 so as to be movable in a longitudinal direction of the shield 20 (i.e., Z axis direction). The hard inner needle 50 made of metal is fixed to a front end of the hub 40. The inner needle 50 has an approximately cylindrical shape, and the leading end thereof is processed to be sharp. One end of a flexible tube 60 made of resin is connected to a rear end of the hub 40. The other end of the tube 60 is connected to, for example, a blood circuit for performing hemodialysis. An O-ring 49 is installed on an outer circumferential face of the hub 40. The O-ring 49 is in close contact with the inner circumferential face of the shield tube 21 and prevents, in the inner cavity of the shield 20, blood that is present on the outer needle 30 side with respect to the O-ring 49 from leaking to the tube 60 side with respect to the O-ring 49. Although there is no particular limitation on the material for the hub 40, a hard material is preferable, and, for example, polycarbonate, polypropylene, polyethylene, and the like can be used. Although there is no particular limitation on the material for the tube 60, a soft material is preferable, and, for example, vinyl chloride and the like can be used.

Figure 3A:
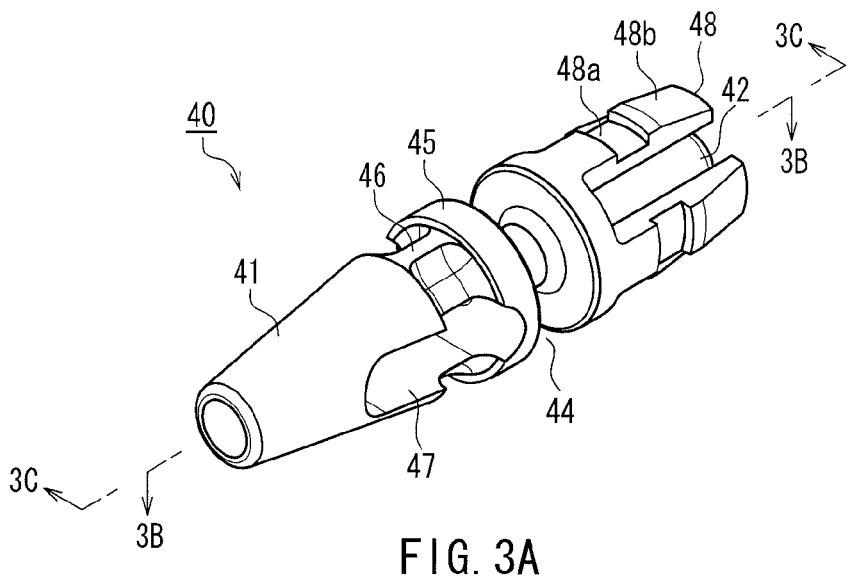
FIG. 3A is a perspective view of a hub used in the indwelling needle device according to Embodiment 1 of the present invention.
Figure 3B:
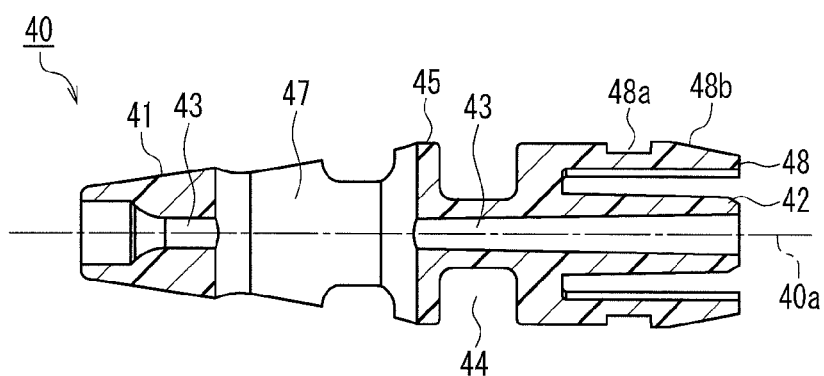
FIG. 3B is a cross-sectional view of the hub taken along a plane containing line 3B-3B in FIG. 3A and seen in the direction of arrows 3B.
Figure 3C:
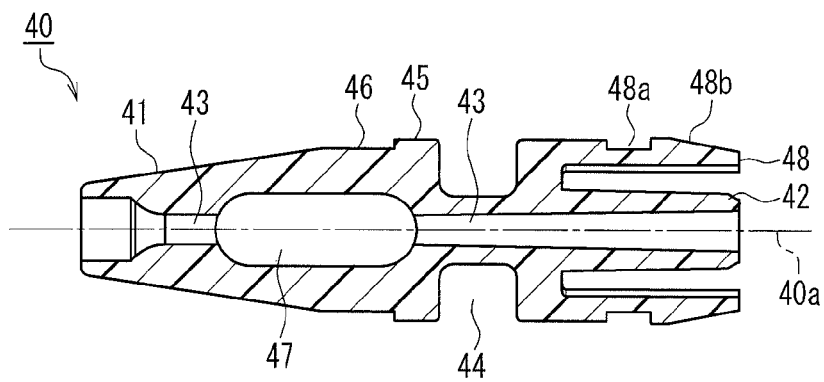
FIG. 3C is a cross-sectional view of the hub taken along a plane containing line 3C-3C in FIG. 3A and seen in the direction of arrows 3C.

FIG. 3A is a perspective view of the hub 40, FIG. 3B is a cross-sectional view of the hub 40 taken along a plane containing line 3B-3B in FIG. 3A and seen in the direction of arrows 3B, and FIG. 3C is a cross-sectional view of the hub 40 taken along a plane containing line 3C-3C in FIG. 3A and seen in the direction of arrows 3C. The cross-section shown in FIG. 3B and the cross-section shown in FIG. 3C are orthogonal to each other. The hub 40 has at its end (front end) a front portion 41 having a circular conical outer face, and has at its other end a rear portion 42 having a cylindrical outer face. A longitudinal penetration path 43 longitudinally penetrates the hub 40 and extends along a central axis 40a of the hub 40 from the front portion 41 to the rear portion 42. As shown in FIG. 2, the inner needle 50 is inserted into the longitudinal penetration path 43 from the front portion 41 side and held by the hub 40. The rear portion 42 is inserted into the tube 60, so that the hub 40 is connected to the tube 60. Thus, the inner needle 50 and the tube 60 are in communication with each other via the longitudinal penetration path 43 of the hub 40.

An annular groove 44 that is continuous in a circumferential direction is formed in the outer circumferential face of the hub 40 in a location between the front portion 41 and the rear portion 42. As shown in FIG. 2, the O-ring 49 is installed in the annular groove 44.

A large diameter portion 45 and a small diameter portion 46 are formed in the outer circumferential face of the hub 40 in respective locations between the annular groove 44 and the front portion 41, in that order from the annular groove 44 side. The small diameter portion 46 is adjacent to the front portion 41, and the outer diameter of the small diameter portion 46 is substantially the same as the largest diameter of the front portion 41 and is smaller than the outer diameter of the large diameter portion 45. A lateral penetration path 47 that laterally penetrates the front portion 41, the small diameter portion 46, and the large diameter portion 45 in their diameter direction (direction orthogonal to the central axis 40a) is formed in these portions. The lateral penetration path 47 intersects and is in communication with the longitudinal penetration path 43.

Four cantilevered elastic pieces 48 are arranged around the rear portion 42 at equiangular intervals with respect to the central axis 40a of the hub 40. The elastic pieces 48 extend approximately parallel to the central axis 40a of the hub 40. A fitting groove 48a and a tapered surface 48b are formed in a face of each elastic piece 48 that is opposite from the rear portion 42. The fitting groove 48a is a recess (groove) extending in the circumferential direction of the hub 40. The tapered surface 48b is adjacent to the fitting groove 48a on a side thereof that is closer to the free end of the elastic piece 48, and constitutes a portion of a circular conical face that has larger outer diameters on the fitting groove 48a side.

In FIGS. 1A, 1B, and 2, the hub 40 is located on the front end side of the inner cavity of the shield 20. In the present invention, this position of the hub 40 relative to the shield 20 is referred to as an "initial position". At the initial position, the inner needle 50 held by the hub 40 penetrates the outer needle 30, and the leading end thereof protrudes to the outside from the leading end of the outer needle 30.

Figure 4A:
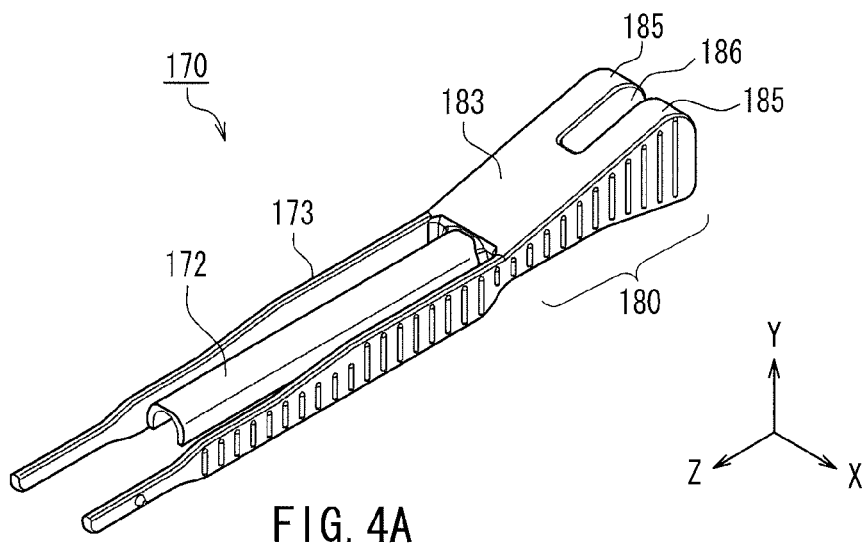
FIG. 4A is a perspective view of a stopper used in the indwelling needle device according to Embodiment 1 of the present invention as seen from above.
Figure 4B:
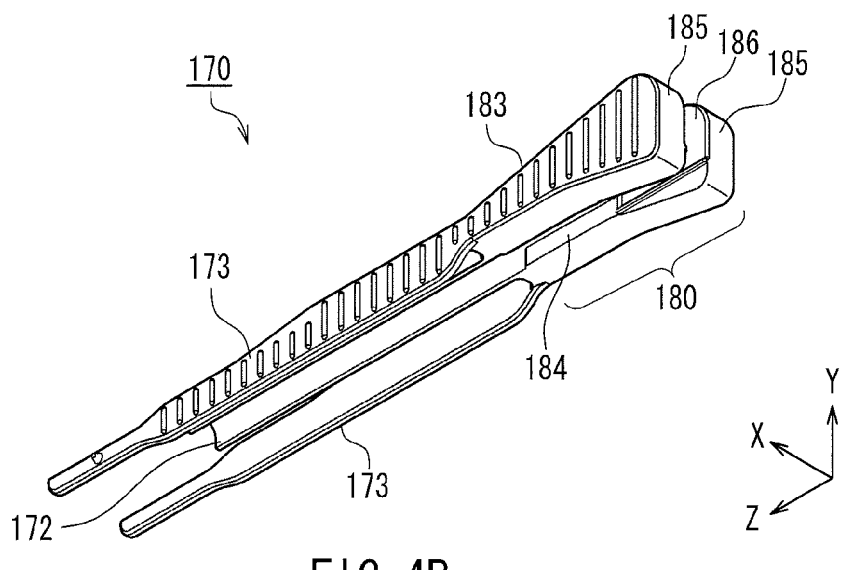
FIG. 4B is a perspective view thereof as seen from below.
Figure 4C:
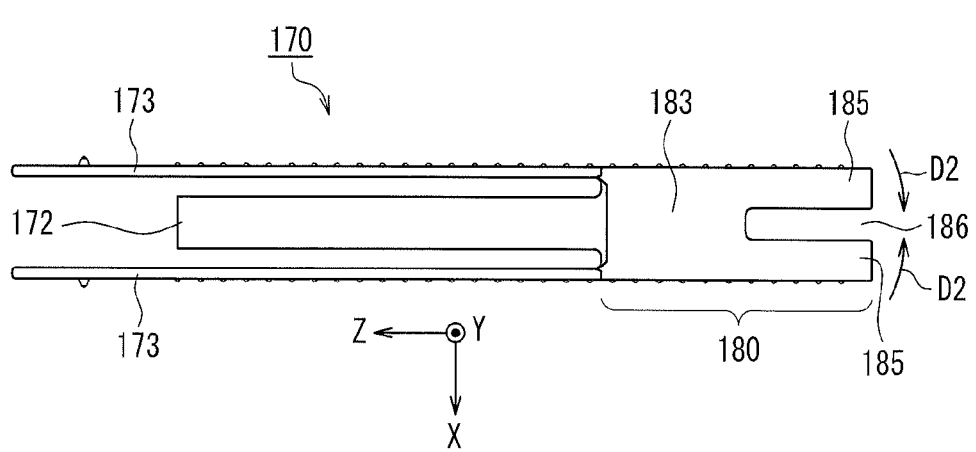
FIG. 4C is a plan view thereof.

In order to maintain the hub 40 at the initial position, a stopper 170 is used. FIG. 4A is a perspective view of the stopper 170 as seen from above, FIG. 4B is a perspective view thereof as seen from below, and FIG. 4C is a plan view thereof. The stopper 170 includes an insertion portion 172, a pair of fixing portions 173, and a base portion 180.

The rear portion of the base portion 180 is divided into a pair of grasping portions 185 along a slit 186 that is formed from the rear end of the base portion 180. The pair of grasping portions 185 face each other in the X axis direction, and can be elastically displaced in mutually approaching orientations D2 (see FIG. 4C).

The front portion of the base portion 180 in which the slit 186 is not formed is referred to as a roof portion 183. As shown in FIG. 4B, a groove 184 that connects the insertion portion 172 and the slit 186 in the form of a straight line and that extends in the Z axis direction is formed on the lower side of the roof portion 183.

The dimension of the base portion 180 in the vertical direction (Y axis direction) is larger at the grasping portions 185 than at the roof portion 183. The upper faces of the roof portion 183 and the grasping portions 185 are formed as an inclined face that is lower toward the insertion portion 172 such that a difference in dimension between the grasping portions 185 and the roof portion 183 gradually changes.

The insertion portion 172 is disposed between the pair of fixing portions 173, and the insertion portion 172 and the pair of fixing portions 173 extend parallel to the Z axis from the roof portion 183 toward the front side. The cross-section of the insertion portion 172 along a plane perpendicular to its longitudinal direction (i.e., plane parallel to the XY plane) is approximately in the shape of a U with an open bottom. The fixing portions 173 are plate-like members having main faces that are parallel to the YZ plane.

As shown in FIGS. 1A, 1B, and 2, the insertion portion 172 of the stopper 170 is inserted into the inner cavity of the shield tube 21 from the rear end of the shield tube 21. When the stopper 170 is inserted into the shield 20 as far as possible, the leading end of the insertion portion 172 hits the rear ends of the elastic pieces 48 of the hub 40, the large diameter portion 45 of the hub 40 in turn hits the rear end of the outer hub 25, and the hub 40 is disposed at the initial position within the inner cavity of the shield 20. The tube 60 connected to the hub 40 is fitted to the insertion portion 172 having an approximately U-shaped cross-section, the groove 184 on the lower side of the roof portion 183, and the slit 186 between the grasping portions 185. The pair of fixing portions 173 of the stopper 170 are located on both sides of the shield tube 21 of the shield 20, and the leading ends of the fixing portions 173 reach the positions of the wings 29a and 29b. The base portion 180 of the stopper 170 is located outside the shield tube 21.

Figure 5:
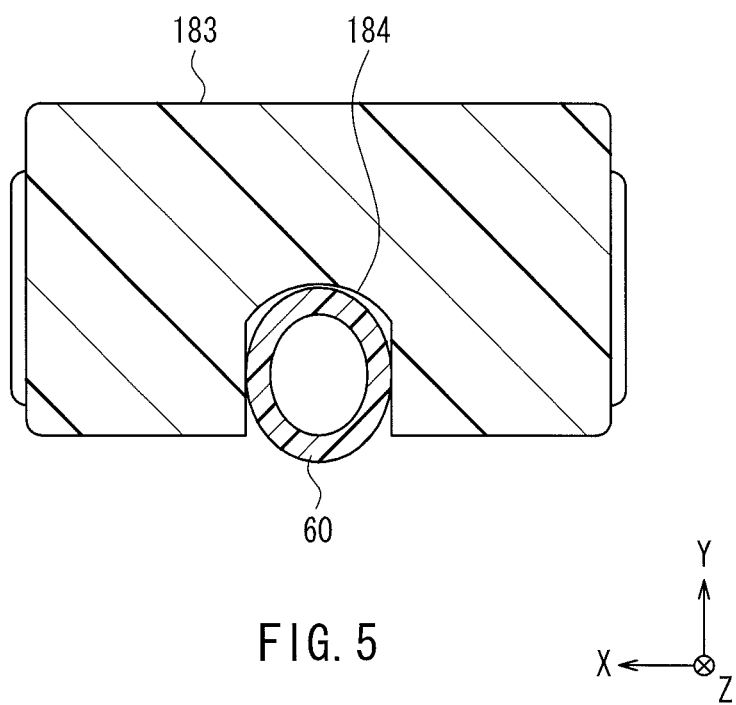
FIG. 5 is a cross-sectional view of the indwelling needle device according to Embodiment 1 of the present invention taken along a vertical plane containing line 5-5 in FIG. 1A and seen in the direction of arrows 5.

FIG. 5 is a cross-sectional view taken along a vertical plane (XY plane) containing line 5-5 in FIG. 1A passing through the roof portion 183, and seen in the direction of arrows 5. For the sake of simplicity, FIG. 5 is provided as an end view in which members behind the cross-section are not shown. The inner circumferential face of the groove 184 of the roof portion 183 has an approximately U-shaped cross-section, and the tube 60 is fitted to the groove 184. Part of the outer circumferential face of the tube 60 facing downward is exposed, and the remainder thereof is covered by the roof portion 183. It is preferable that, as shown in FIG. 5, part of the exposed lower outer circumferential face of the tube 60 slightly protrudes downward from the lower face of the roof portion 183. It is preferable that the depth (dimension in the Y axis direction) of the groove 184 is equal to or smaller than the outer diameter of the tube 60. Furthermore, it is preferable that the width (dimension in the X axis direction) of the groove 184 is equal to or smaller than the outer diameter of the tube 60.

Hereinafter, operational methods and actions of the thus configured indwelling needle device 100 of Embodiment 1 will be described.

The inner needle 50 and the outer needle 30 are inserted into a blood vessel of the patient in a state in which the inner needle 50 protrudes from the leading end of the outer needle 30 as shown in FIGS. 1A, 1B, and 2. During puncture, the inner needle 50 receives a reaction force. Thus, the inner needle 50 and the hub 40 holding the inner needle 50 have to be prevented from being moved toward the rear side by this reaction force relative to the outer needle 30 and the shield 20. The leading end of the insertion portion 172 of the stopper 170 abuts against the rear end (the elastic pieces 48) of the hub 40, and restricts the movement of the hub 40. It is necessary that, during puncture, the operator grips the indwelling needle device 100 such that the stopper 170 does not move relative to the shield 20. Such gripping methods generally include the following four methods.

In a first gripping method, the roof portion 183 of the stopper 170 is gripped with two fingers (e.g., the thumb and the index finger) in the vertical direction (Y axis direction) as indicated by arrows H11 in FIG. 6A. As shown in FIG. 5, the outer circumferential face of the tube 60 is partially exposed on the lower side of the roof portion 183. Thus, according to the first gripping method, the roof portion 183 and the tube 60 can be gripped together.

In a second gripping method, the pair of grasping portions 185 of the stopper 170 are gripped with two fingers in the horizontal direction (X axis direction) as indicated by arrows H12 in FIG. 6B. Examples of the methods for gripping the pair of grasping portions 185 include a method of gripping the pair of grasping portions 185 with the thumb and the middle finger and placing the index finger on the upper face of the shield 20, and a method of gripping the pair of grasping portions 185 with the thumb and the index finger. The former method is preferable because the indwelling needle device 100 can be held stably. Since the pair of grasping portions 185 are elastically displaced by the gripping force at that time in mutually approaching orientations (see arrows D2 in FIG. 4C), the pair of grasping portions 185 grasp the tube 60 located therebetween. Thus, according to the second gripping method, the pair of grasping portions 185 and the tube 60 can be gripped together.

In a third gripping method, the pair of fixing portions 173 of the stopper 170 are gripped with two fingers (e.g., the thumb and the index finger) in the horizontal direction (X axis direction) as indicated by arrows H13 in FIG. 6B. The pair of fixing portions 173 are elastically deformed easily by the gripping force at that time in mutually approaching orientations, and brought into close contact with the outer circumferential face of the shield tube 21. Thus, according to the third gripping method, the pair of fixing portions 173 and the shield tube 21 can be gripped together.

In a fourth gripping method, the wings 29a and 29b are bent upward so as to overlap each other, and are gripped with two fingers (e.g., the thumb and the index finger) in the horizontal direction (X axis direction) (not shown). At that time, the pair of fixing portions 173 are sandwiched and fixed between the wings 29a and 29b and the shield tube 21. Thus, according to the fourth gripping method, the pair of fixing portions 173 and the shield tube 21 in addition to the wings 29a and 29b can be gripped together.

After the inner needle 50 and the outer needle 30 are inserted into a blood vessel of the patient in a state in which the indwelling needle device 100 is gripped using any one of the above-described methods, the stopper 170 is pulled out of the shield 20, and simultaneously or subsequently, the tube 60 is pulled from the shield 20. This operation will be described later in detail. Since the hub 40 is connected to the front end of the tube 60, pulling the tube 60 causes the hub 40 and the inner needle 50 held by the hub 40 to move toward the rear side relative to the shield 20.

The engagement protrusion 22 is formed in the inner circumferential face of the shield tube 21 in the vicinity of its rear end. The hub 40 moves to the engagement protrusion 22, and the tapered surfaces 48b formed in the respective outer faces of the elastic pieces 48 of the hub 40 slide on the engagement protrusion 22. At this time, the elastic pieces 48 undergo elastic deformation to the rear portion 42 side. Then, when the tapered surfaces 48b have got over the engagement protrusion 22, the elastic pieces 48 undergo elastic recovery, and the engagement protrusion 22 is fitted to the fitting grooves 48a. In the present invention, the position of the hub 40 relative to the shield 20 when the fitting grooves 48a and the engagement protrusion 22 are fitted to each other is referred to as a "retracted position".

Figure 7:
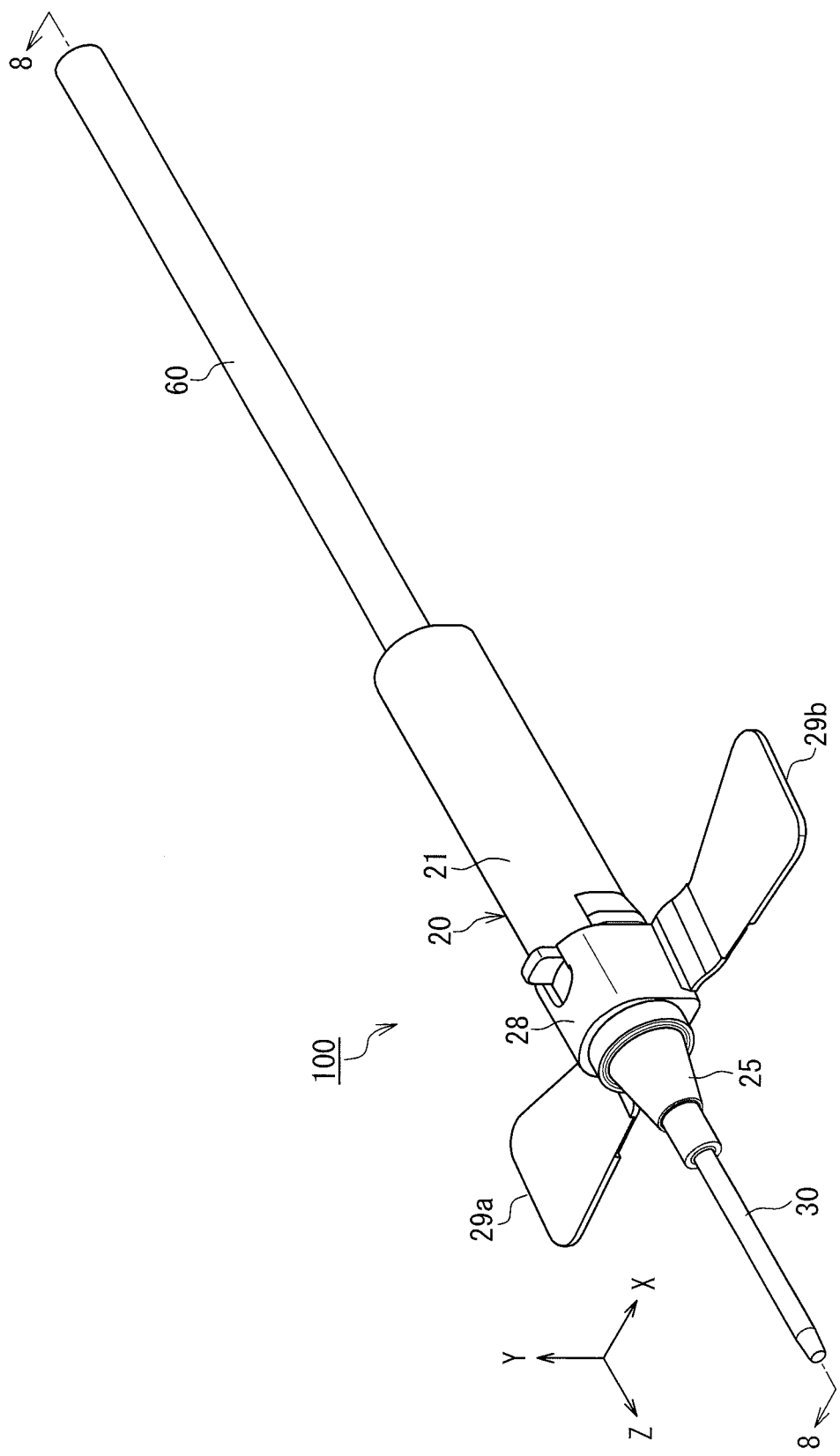
FIG. 7 is a perspective view, as seen from above, of the indwelling needle device according to Embodiment 1 of the present invention with the hub being at the retracted position.
Figure 8:
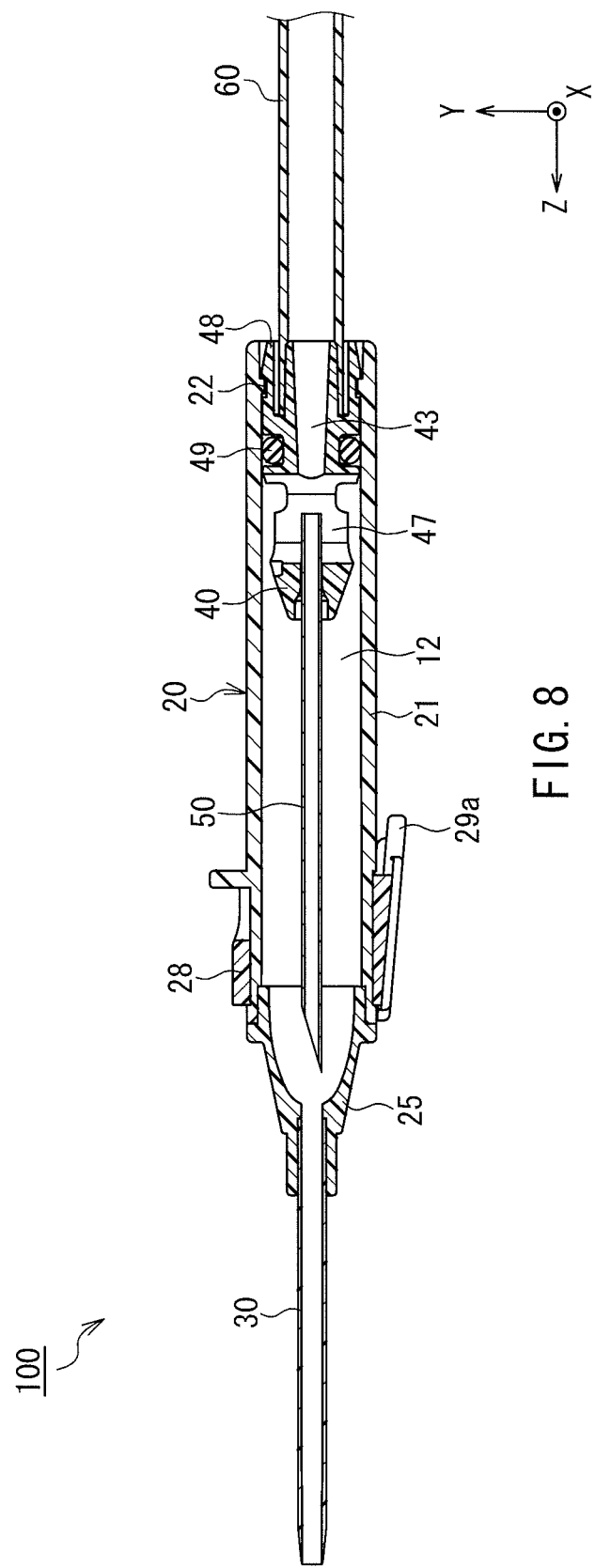
FIG. 8 is a cross-sectional view of the indwelling needle device according to Embodiment 1 of the present invention taken along a vertical plane containing line 8-8 in FIG. 7 and seen in the direction of arrows 8.

FIG. 7 is a perspective view, as seen from above, of the indwelling needle device 100 with the hub 40 at the retracted position. FIG. 8 is a cross-sectional view of the indwelling needle device 100 taken along a vertical plane (YZ plane) containing line 8-8 in FIG. 7 and seen in the direction of arrows 8.

As shown in FIG. 8, when the hub 40 is at the retracted position the fitting grooves 48a (see FIGS. 3A, 3B, and 3C) of the hub 40 and the engagement protrusion 22 of the shield tube 21 are fitted to each other. Moreover, the inner needle 50 held by the hub 40 has been pulled out of the outer needle 30 and is housed within the inner cavity of the shield 20.

When compared with the initial position (see FIGS. 1A, 1B, and 2), at the retracted position, the cross-sectional area of the flow channel within the outer needle 30 is increased by an amount corresponding to the cross-sectional area of the inner needle 50, and accordingly the amount of blood flowing into the indwelling needle device 100 is increased. Furthermore, at the retracted position, the flow channel from the outer needle 30 to the tube 60 includes two flow channels, that is, a first flow channel sequentially passing through the inner cavity of the inner needle 50 and the longitudinal penetration path 43 of the hub 40 and a second flow channel sequentially passing through a space 12 between the inner face of the shield 20 and the respective outer faces of the inner needle 50 and the hub 40, the lateral penetration path 47 of the hub 40, and the longitudinal penetration path 43 of the hub 40, and accordingly a greater amount of blood can flow into the indwelling needle device 100.

In this state, an adhesive tape is attached to the skin of the patient over the wings 29a and 29b, and the indwelling needle device 100 is fixed to the patient. Only the outer needle 30 is left inside the patient in a state in which it is inserted in the patient. At the retracted position, the hard inner needle 50 is not present in the flexible outer needle 30, and therefore, even if the position of the indwelling needle device 100 relative to the patient changes due to movement of the patient or the like, the outer needle 30 does not injure the blood vessel and the like of the patient.

When the necessary treatment has been finished, the adhesive tape that fixes the wings 29a and 29b is removed from the patient, and the outer needle 30 is withdrawn from the patient. Even when the tube 60 is pushed or pulled relative to the shield 20, the fitted state in which the fitting grooves 48a of the hub 40 and the engagement protrusion 22 of the shield tube 21 are fitted to each other is not released. That is to say, the inner needle 50 cannot be caused to again protrude from the leading end of the outer needle 30, and inner needle 50 cannot be withdrawn from the shield 20 together with the hub 40. Accordingly, accidental puncture with the hard inner needle 50 and accidental reuse of the used indwelling needle device 10 are prevented. The used indwelling needle device 100 will be discarded.

Hereinafter, an operation for moving the hub 40 to the retracted position as shown in FIGS. 7 and 8 after the inner needle 50 and the outer needle 30 are inserted into a blood vessel of the patient will be described.

In order to move the hub 40 from the initial position (see FIGS. 1A, 1B, and 2) to the retracted position (see FIGS. 7 and 8), it is necessary to pull out (remove) the stopper 170 from the shield 20. In order to remove the stopper 170 from the state seen in FIGS. 1A and 1B, it is necessary for the operator to grip the portion of the stopper 170 exposed out of the shield 20. Note that, if the pair of fixing portions 173 are gripped as in the third gripping method (arrows H13 in FIG. 6B), not only the pair of fixing portions 173 but also the shield tube 21 is gripped together as described above, and, thus, the stopper 170 cannot be removed from the shield 20. Accordingly, the operator will inevitably grip the base portion 180.

For example, the roof portion 183 of the base portion 180 can be gripped in the vertical direction (Y axis direction) as in the first gripping method (arrows H11 in FIG. 6A). In this case, as described above, the roof portion 183 and the tube 60 can be gripped together. Accordingly, pulling the stopper 170 from the shield 20 causes the tube 60 to be pulled together with the stopper 170.

Alternatively, the pair of grasping portions 185 of the base portion 180 can be gripped in the horizontal direction (X axis direction) as in the second gripping method (arrows H12 in FIG. 6B). In this case, as described above, the pair of grasping portions 185 are elastically displaced and grasp the tube 60 located therebetween. Accordingly, pulling the stopper 170 from the shield 20 causes the tube 60 to be pulled together with the stopper 170.

As described above, according to Embodiment 1, when the base portion 180 is gripped in the vertical direction or in the horizontal direction and is withdrawn from the shield 20, the tube 60 can be pulled together with the stopper 170.

Figure 18A:
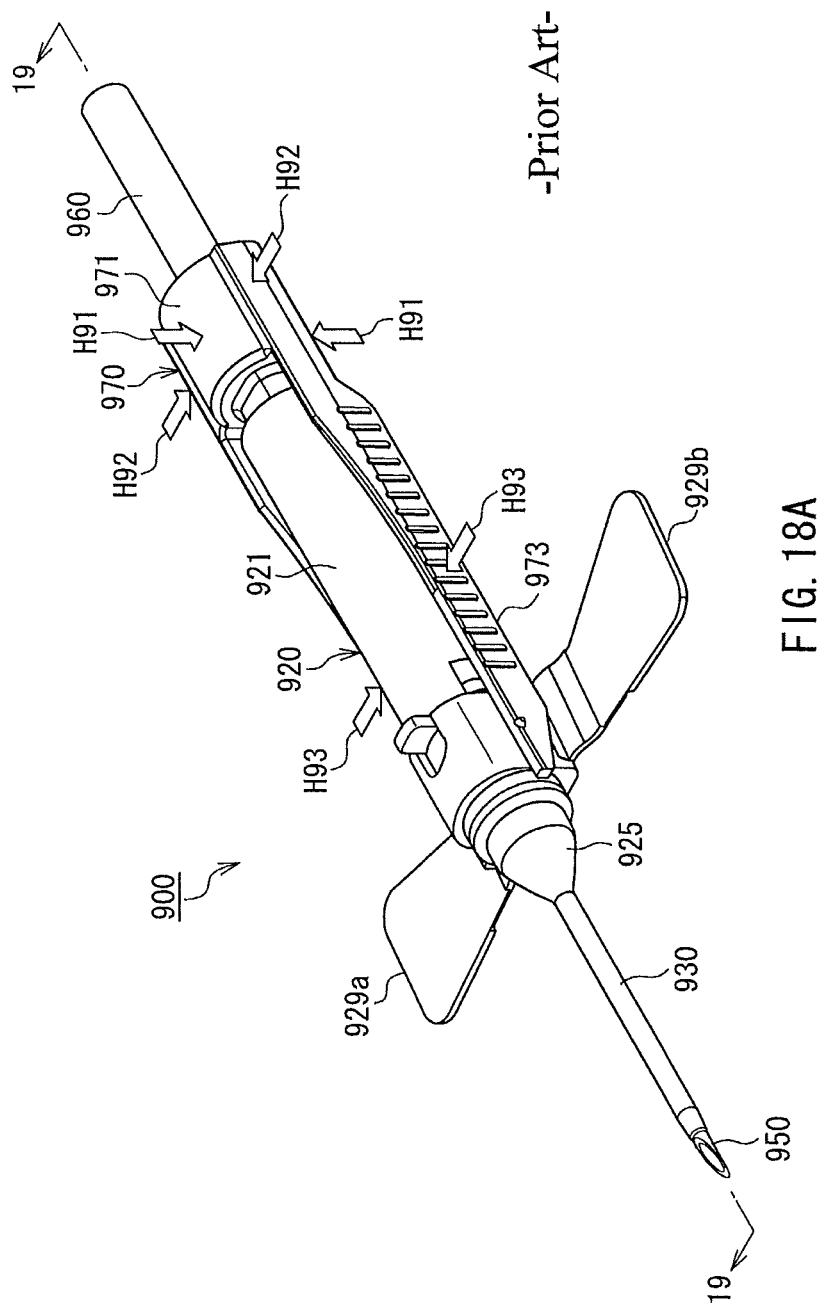
FIG. 18A is a perspective view of a conventional indwelling needle device as seen from above.
Figure 19:
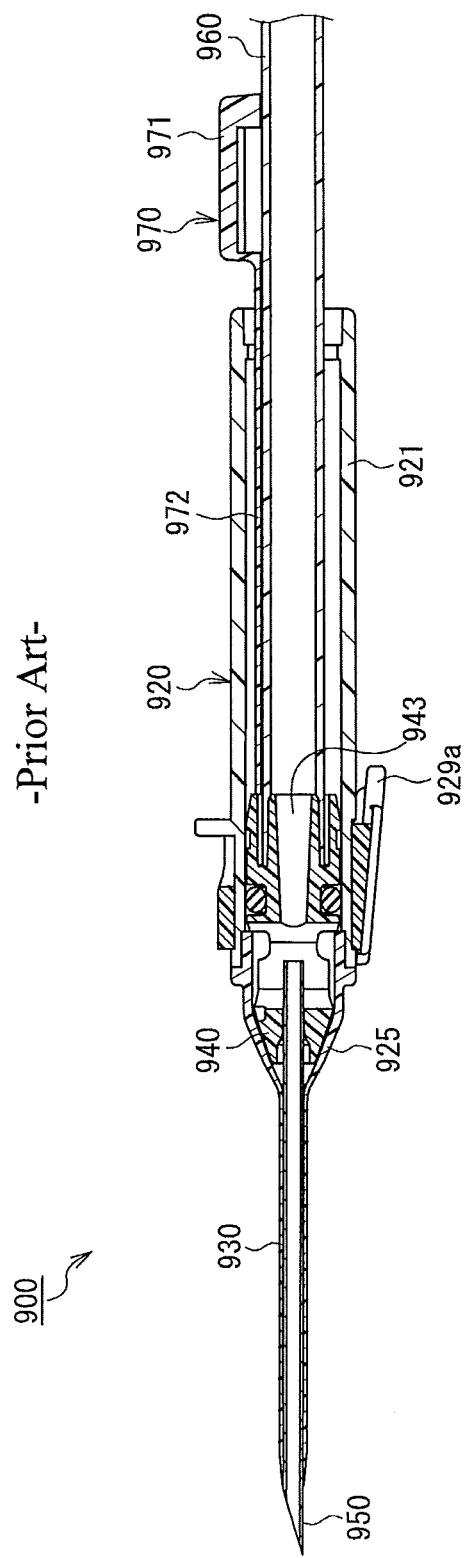
FIG. 19 is a cross-sectional view of the conventional indwelling needle device taken along a vertical plane containing line 19-19 in FIG. 18A and seen in the direction of arrows 19.
Figure 20:
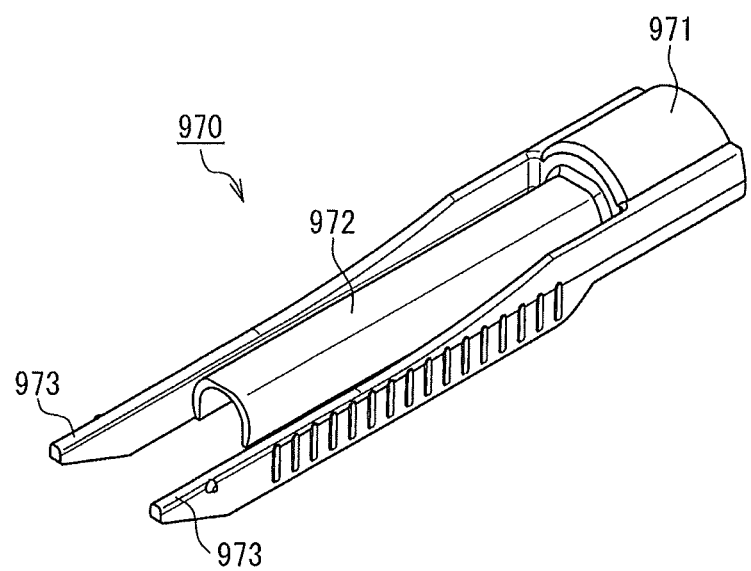
FIG. 20 is a perspective view of a stopper used in the conventional indwelling needle device shown in FIGS. 18A and 18B.

On the other hand, according to the conventional indwelling needle device 900 described above, a shape corresponding to the slit 186 of Embodiment 1 is not formed in the base end portion 971, and, thus, when the base end portion 971 is gripped in the horizontal direction (see arrows H92 in FIG. 18A), the tube 960 cannot be gripped together with the stopper 970. Accordingly, only the stopper 970 can be pulled out of the shield 920 without changing the positions of the hub 940 and the inner needle 950. As a result, there is a possibility of the operator forgetting to pull the tube 960 to house the inner needle 950 within the shield 920.

Contrary to the conventional indwelling needle device 900, in Embodiment 1, regardless of whether the base portion 180 is gripped either in the vertical direction (see arrows H11 in FIG. 6A) or in the horizontal direction (see arrows H12 in FIG. 6B), pulling out the stopper 170 can cause the hub 40 simultaneously to move to the retracted position (see FIGS. 7 and 8). Accordingly, the possibility can be reduced of an operational error occurring in which the operator pulls out only the stopper 170 after the puncture and forgets to house the inner needle 50 within the shield 20.

Furthermore, according to the conventional indwelling needle device 900 described above, when puncture has been performed in a state in which the base end portion 971 is gripped in the horizontal direction (see arrows H92 in FIG. 18A), it is necessary to change the grip position after the puncture in order to house the inner needle 950 within the shield 920. On the other hand, in Embodiment 1, when puncture with the inner needle 50 and the outer needle 30 has been performed in a state in which the base portion 180 is gripped in the vertical direction (the first gripping method, see arrows H11 in FIG. 6A) or in the horizontal direction (the second gripping method, see arrows H12 in FIG. 6B), the inner needle 50 can be housed within the shield 20 after the puncture, without changing the grip position. Accordingly, a series of operations can be performed quickly and efficiently.

In the foregoing example, as shown in FIG. 5, part of the outer circumferential face of the tube 60 slightly protrudes downward from the lower face of the roof portion 183. In the first gripping method (see arrows H11 in FIG. 6A), this configuration is advantageous to grip the tube 60 and the stopper 170 together while preventing the tube 60 from slipping relative to the stopper 170. Accordingly, the possibility can be further reduced of an operational error occurring in which the operator forgets to house the inner needle 50 within the shield 20.

In the foregoing example, as shown in FIGS. 4A, 4B, and 6A, the dimension of the grasping portions 185 in the vertical direction (Y axis direction) is larger than that of the roof portion 183. In the second gripping method (see arrows H12 in FIG. 6B), this configuration is advantageous to stably grip the indwelling needle device 100 including the stopper 170.

Moreover, in the foregoing example, as shown in FIG. 4A, the upper face of the roof portion 183 is inclined so as to be gradually lower from the grasping portions 185 toward the insertion portion 172. In the second gripping method (see arrows H12 in FIG. 6B), this configuration is advantageous to pull the stopper 170 out of the shield 20. That is to say, according to the second gripping method, the stopper 170 can be pulled out of the shield 20, by touching a rear end 21r (see FIGS. 2 and 6A) of the shield tube 21 with the index finger while gripping the pair of grasping portions 185 with the thumb and the middle finger, and then moving the index finger so as to push the shield tube 21 toward the front side. At that time, if the upper face of the roof portion 183 is inclined as described above, as can be easily seen from FIGS. 2 and 6A, the rear end 21r of the shield tube 21 can relatively protrude with respect to the upper face of the roof portion 183, and, thus, a force easily can be applied from the index finger to the rear end 21r of the shield tube 21.

In the foregoing example, as shown in FIG. 5, the width (dimension in the X axis direction) of the groove 184 is equal to or smaller than the outer diameter of the tube 60. Accordingly, the tube 60 is elastically compressed and deformed in the X axis direction by the inner circumferential face of the groove 184, and slippage between the tube 60 and the stopper 170 is reduced. Accordingly, when the stopper 170 is pulled out of the shield 20, the tube 60 can be pulled together with the stopper 170.

In the foregoing example, the roof portion 183 and the grasping portions 185 are arranged in that order from the insertion portion 172 side. Therefore, the grasping portions 185 can be arranged at the rear end of the stopper 170 and cantilevered thereby. Accordingly, the amount of the grasping portions 185 to be elastically displaced easily can be increased. As a result, when the base portion 180 is gripped in the horizontal direction (see arrows H12 in FIG. 6B), the tube 60 can be more reliably grasped by the pair of grasping portions 185.

Embodiment 2

An indwelling needle device 200 of Embodiment 2 is different from the indwelling needle device 100 of Embodiment 1 in the configuration of the stopper. In the drawings used in the description below, the same constituent members as those in the indwelling needle device 100 of Embodiment 1 are denoted by the same reference numerals, and a description thereof has been omitted. Hereinafter, the indwelling needle device 200 of Embodiment 2 will be described mainly regarding aspects different from those in Embodiment 1.

Figure 9A:
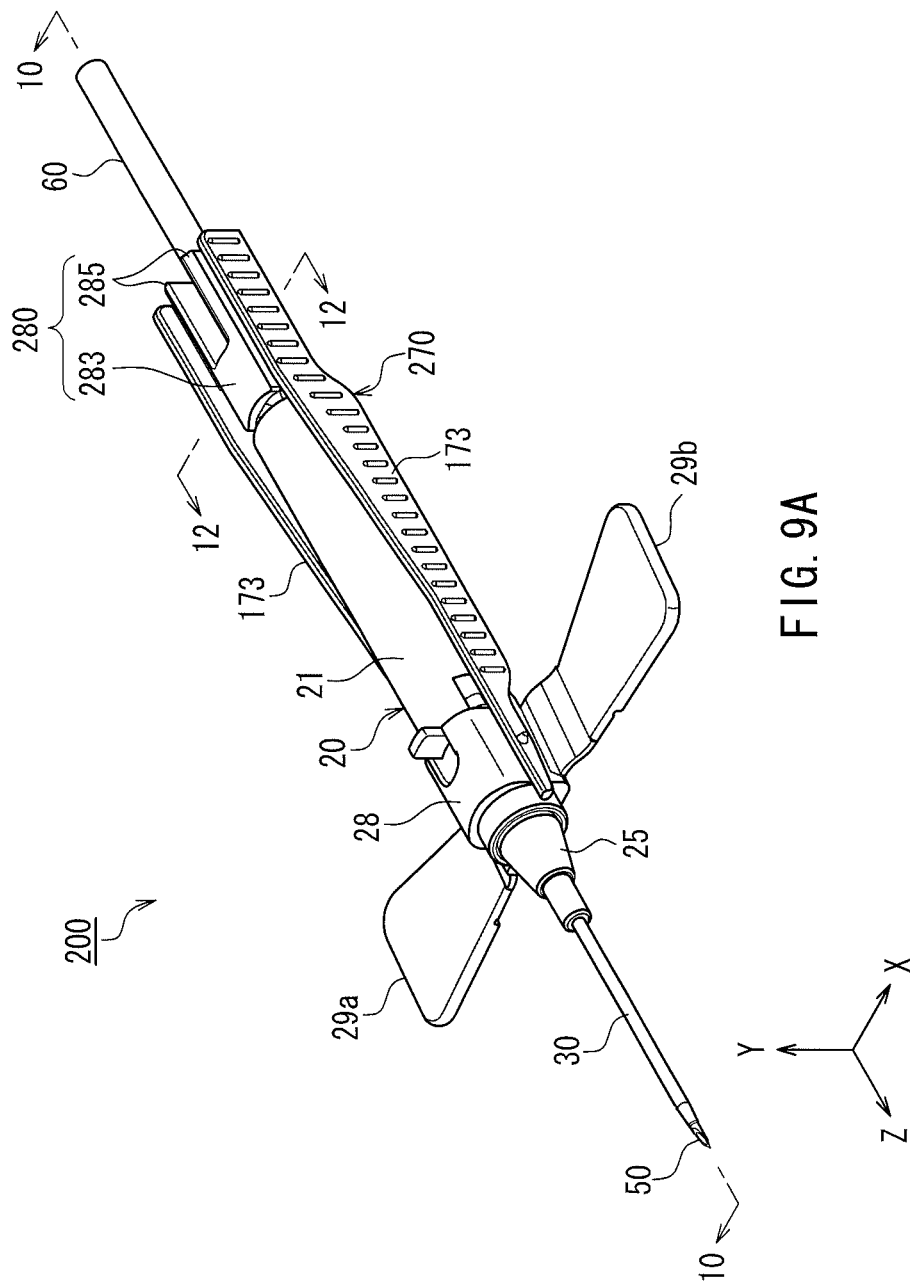
FIG. 9A is a perspective view of an indwelling needle device according to Embodiment 2 of the present invention as seen from above.
Figure 9B:
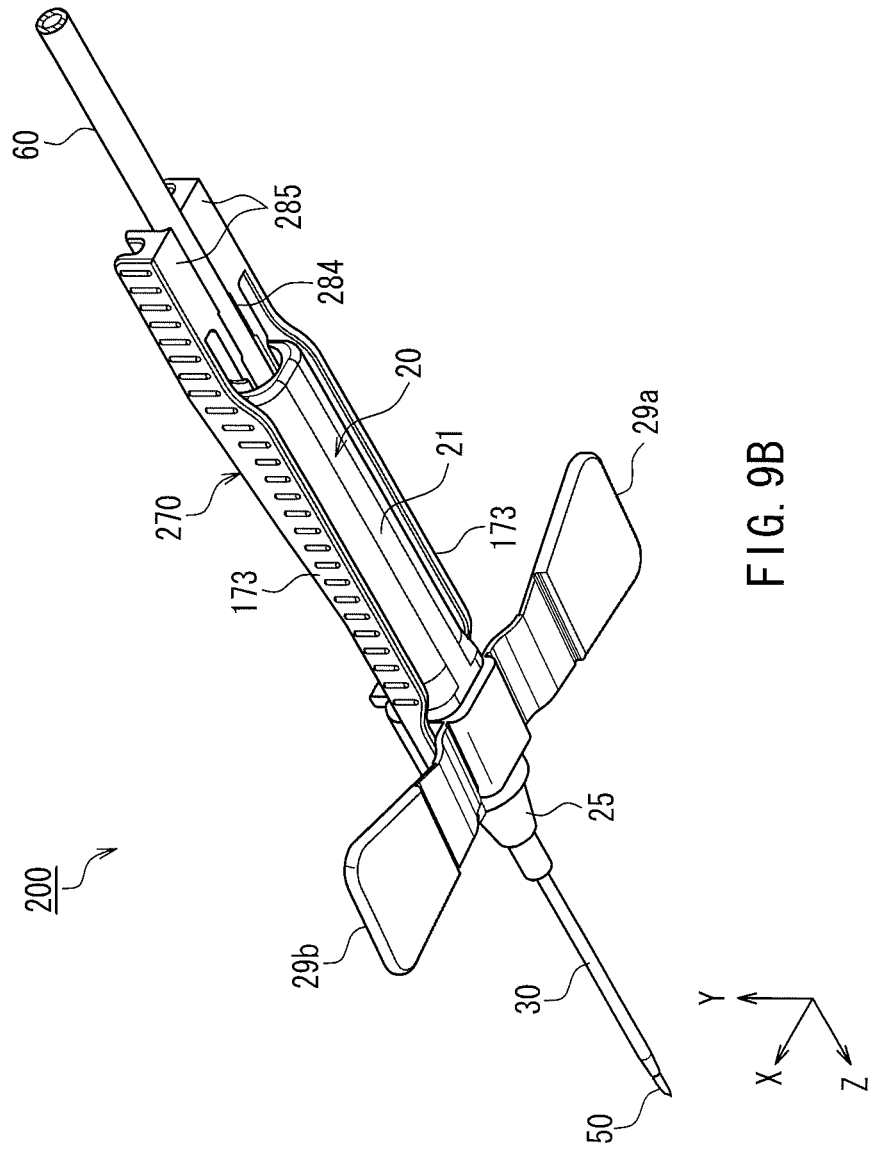
FIG. 9B is a perspective view of the indwelling needle device according to Embodiment 2 of the present invention as seen from below.
Figure 10:
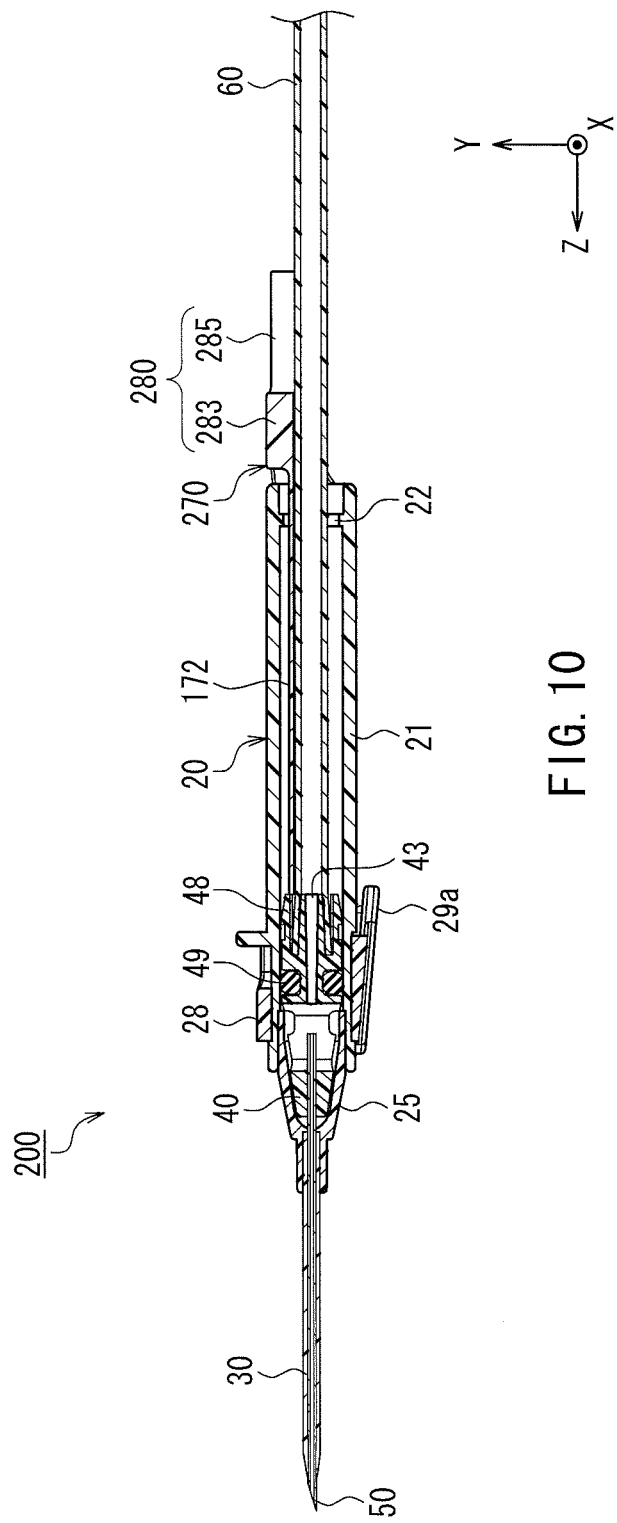
FIG. 10 is a cross-sectional view of the indwelling needle device according to Embodiment 2 of the present invention taken along a vertical plane containing line 10-10 in FIG. 9A and seen in the direction of arrows 10.
Figure 11A:
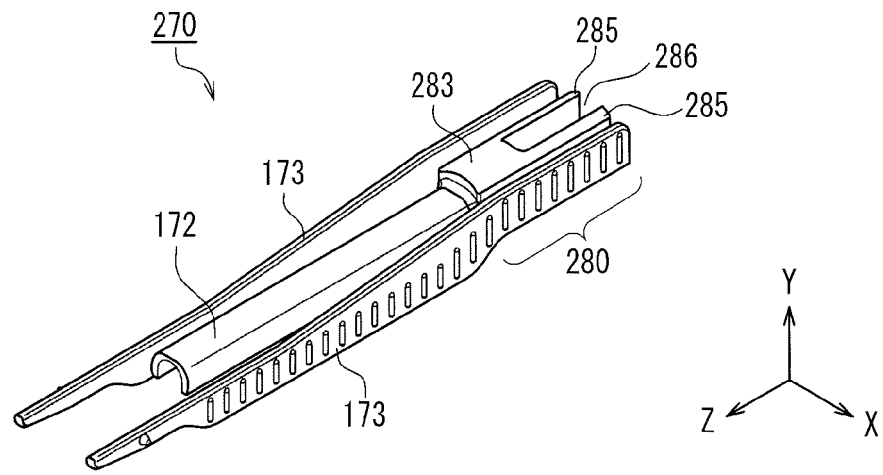
FIG. 11A is a perspective view of a stopper used in the indwelling needle device according to Embodiment 2 of the present invention as seen from above.
Figure 11B:
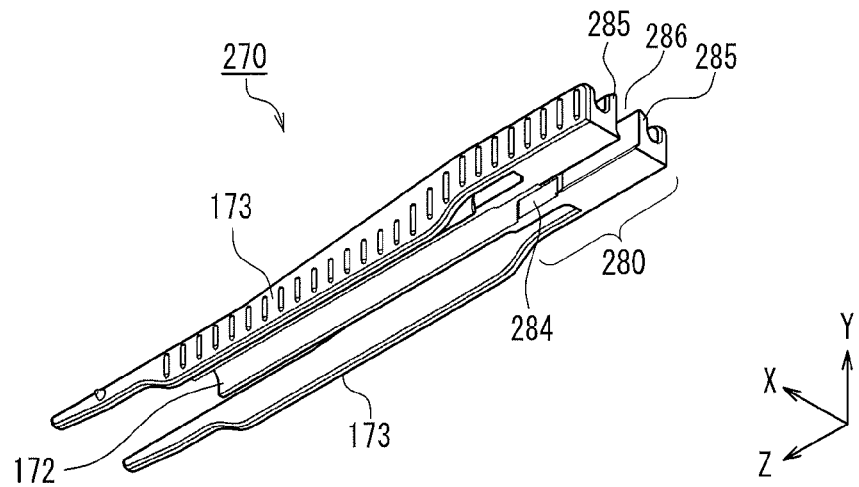
FIG. 11B is a perspective view thereof as seen from below.
Figure 11C:
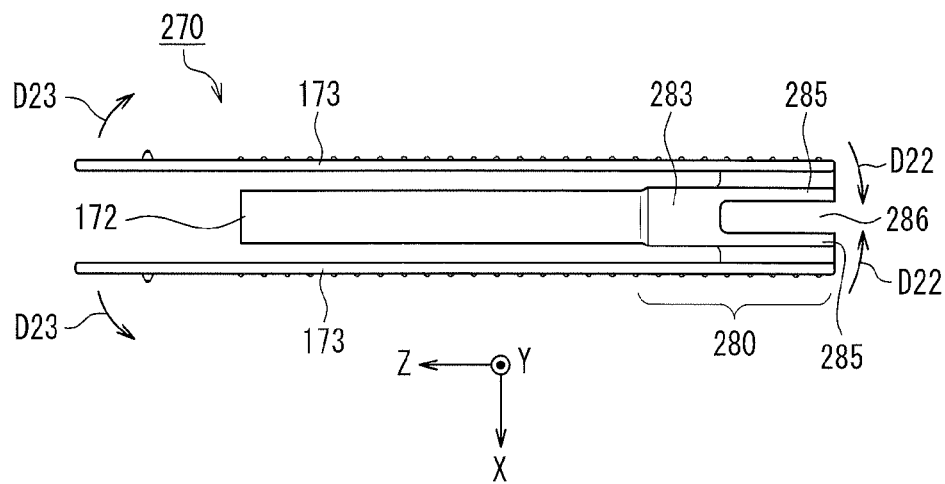
FIG. 11C is a plan view thereof.

FIG. 9A is a perspective view, as seen from above, of the indwelling needle device 200 according to Embodiment 2 of the present invention with the hub 40 being at the initial position, and FIG. 9B is a perspective view thereof as seen from below. FIG. 10 is a cross-sectional view of the indwelling needle device 200 taken along a vertical plane (YZ plane) containing line 10-10 in FIG. 9A and seen in the direction of arrows 10. In Embodiment 2, in order to position and maintain the hub 40 at the initial position, a stopper 270 is used as in Embodiment 1. FIG. 11A is a perspective view of the stopper 270 as seen from above, FIG. 11B is a perspective view thereof as seen from below, and FIG. 11C is a plan view thereof. The stopper 270 of Embodiment 2 includes the insertion portion 172 having an approximately U-shaped cross-section, the pair of plate-like fixing portions 173, and a base portion 280.

The rear portion of the base portion 280 is divided into a pair of grasping portions 285 along a slit 286 that is formed from the rear end of the base portion 280. The pair of grasping portions 285 face each other in the X axis direction, and can be elastically displaced in mutually approaching orientations D22 (see FIG. 11C).

The front portion of the base portion 280 in which the slit 286 is not formed is referred to as a roof portion 283. As shown in FIG. 11B, a groove 284 that connects the insertion portion 172 and the slit 286 in the form of a straight line and that extends in the Z axis direction is formed on the lower side of the roof portion 283.

As in Embodiment 1, the dimension of the base portion 280 in the vertical direction (Y axis direction) may be larger at the grasping portions 285 than at the roof portion 283. Furthermore, the upper face of the roof portion 283 (and the upper face of the grasping portions 285) may be inclined so as to be lower toward the insertion portion 172.

The insertion portion 172 extends parallel to the Z axis from the roof portion 183 toward the front side. Meanwhile, contrary to Embodiment 1, the pair of fixing portions 173 extend along the Z axis from the pair of grasping portions 285. Accordingly, as shown in FIG. 11C, when the pair of grasping portions 285 are displaced in the mutually approaching orientations D22, the front ends of the pair of fixing portions 173 are displaced in mutually separating orientations D23.

As shown in FIGS. 9A, 9B, and 10, the insertion portion 172 of the stopper 270 is inserted into the inner cavity of the shield tube 21 from the rear end of the shield tube 21. As in Embodiment 1, when the leading end of the insertion portion 172 pushes the hub 40 toward the front side, the hub 40 can be disposed at the initial position within the inner cavity of the shield 20. The tube 60 connected to the hub 40 is fitted to the insertion portion 172 having an approximately U-shaped cross-section, the groove 284 on the lower side of the roof portion 283, and the slit 286 between the grasping portions 285. The base portion 280 is located outside the shield tube 21.

FIG. 12 is a cross-sectional view taken along a vertical plane (XY plane) containing line 12-12 in FIG. 9A passing through the roof portion 283, and seen in the direction of arrows 12. For the sake of simplicity, FIG. 12 is provided as an end view in which members behind the cross-section are not shown. The inner circumferential face of the groove 284 of the roof portion 283 has an approximately U-shaped cross-section, and the tube 60 is fitted to the groove 284. Part of the outer circumferential face of the tube 60 facing downward is exposed, and the remainder thereof is covered by the roof portion 283. It is preferable that, as shown in FIG. 12, part of the exposed lower outer circumferential face of the tube 60 slightly protrudes downward from the lower face of the roof portion 283.

The operational methods of the thus configured indwelling needle device 200 of Embodiment 2 are the same as those of the indwelling needle device 100 of Embodiment 1.

That is to say, the inner needle 50 and the outer needle 30 are inserted into a blood vessel of the patient in a state in which the hub 40 is maintained at the initial position (see FIGS. 9A, 9B, and 10). The methods for gripping the indwelling needle device 200 at this time may be the same as the first to fourth gripping methods described in Embodiment 1. FIGS. 13A and 13B show typical grip positions of the indwelling needle device 200. In the first gripping method, the roof portion 283 of the stopper 270 is gripped with two fingers in the vertical direction (Y axis direction) as indicated by arrows H21 in FIG. 13A. In the second gripping method, the pair of grasping portions 285 of the stopper 270 are gripped with two fingers in the horizontal direction (X axis direction) as indicated by arrows H22 in FIG. 13B. In the third gripping method, the pair of fixing portions 273 of the stopper 270 are gripped with two fingers in the horizontal direction (X axis direction) as indicated by arrows H23 in FIG. 13B. In the fourth gripping method, the wings 29a and 29b are bent upward so as to overlap each other, and are gripped with two fingers in the horizontal direction (X axis direction) (not shown).

After the inner needle 50 and the outer needle 30 are inserted into a blood vessel of the patient, the hub 40 is moved to the retracted position (see FIGS. 7 and 8). Thus, it is necessary to pull the stopper 270 out of the shield 20, and to pull the tube 60 from the shield 20. In order to pull the stopper 270 out of the shield 20, it is necessary for the operator to grip the base portion 280 as in Embodiment 1.

For example, the roof portion 283 of the base portion 280 can be gripped in the vertical direction (Y axis direction) as in the first gripping method (arrows H21 in FIG. 13A). As shown in FIG. 12, the outer circumferential face of the tube 60 is partially exposed on the lower side of the roof portion 283, and, thus, the roof portion 283 and the tube 60 can be gripped together. Accordingly, when the stopper 270 is pulled from the shield 20, the tube 60 can be pulled together with the stopper 270.

Alternatively, the pair of grasping portions 285 of the base portion 280 can be gripped in the horizontal direction (X axis direction) as in the second gripping method (arrows H22 in FIG. 13B). In this case, the pair of grasping portions 285 are elastically displaced and grasp the tube 60 located therebetween. Accordingly, when the stopper 270 is pulled from the shield 20, the tube 60 can be pulled together with the stopper 270.

As described above, when the base portion 280 is gripped in the vertical direction or in the horizontal direction and is withdrawn from the shield 20, the tube 60 can be pulled together with the stopper 270, as in Embodiment 1. Accordingly, the possibility can be reduced of an operational error occurring in which the operator pulls out only the stopper 270 after the puncture and forgets to house the inner needle 50 within the shield 20.

Furthermore, when puncture with the inner needle 50 and the outer needle 30 has been performed in a state in which the base portion 280 is gripped in the vertical direction (the first gripping method, see arrows H21 in FIG. 13A) or in the horizontal direction (the second gripping method, see arrows H22 in FIG. 13B), the inner needle 50 can be housed within the shield 20 after the puncture, without changing the grip position. Accordingly, a series of operations can be performed quickly and efficiently.

With the stopper 270 of Embodiment 2, as described with reference to FIG. 11C, the elastic displacement of the pair of grasping portions 285 in the orientations D22 can cause the pair of fixing portions 173 to be displaced in the orientations D23. Accordingly, in the case of applying the second gripping method (see arrows H22 in FIG. 13B), interference can be avoided between the fixing portions 173 and the shield 20 when inserting the insertion portion 172 into the shield 20 and when pulling the stopper 270 out of the shield 20.

Embodiment 2 is same as Embodiment 1 except for the aspects described above. The various modified example described in Embodiment 1 can be applied also to Embodiment 2.

Embodiment 3

An indwelling needle device 300 of Embodiment 3 is different from the indwelling needle device 100 of Embodiment 1 in the configuration of the stopper. In the drawings used in the description below, the same constituent members as those in the indwelling needle device 100 of Embodiment 1 are denoted by the same reference numerals, and a description thereof has been omitted. Hereinafter, the indwelling needle device 300 of Embodiment 3 will be described mainly regarding aspects different from those in Embodiment 1.

Figure 14A:
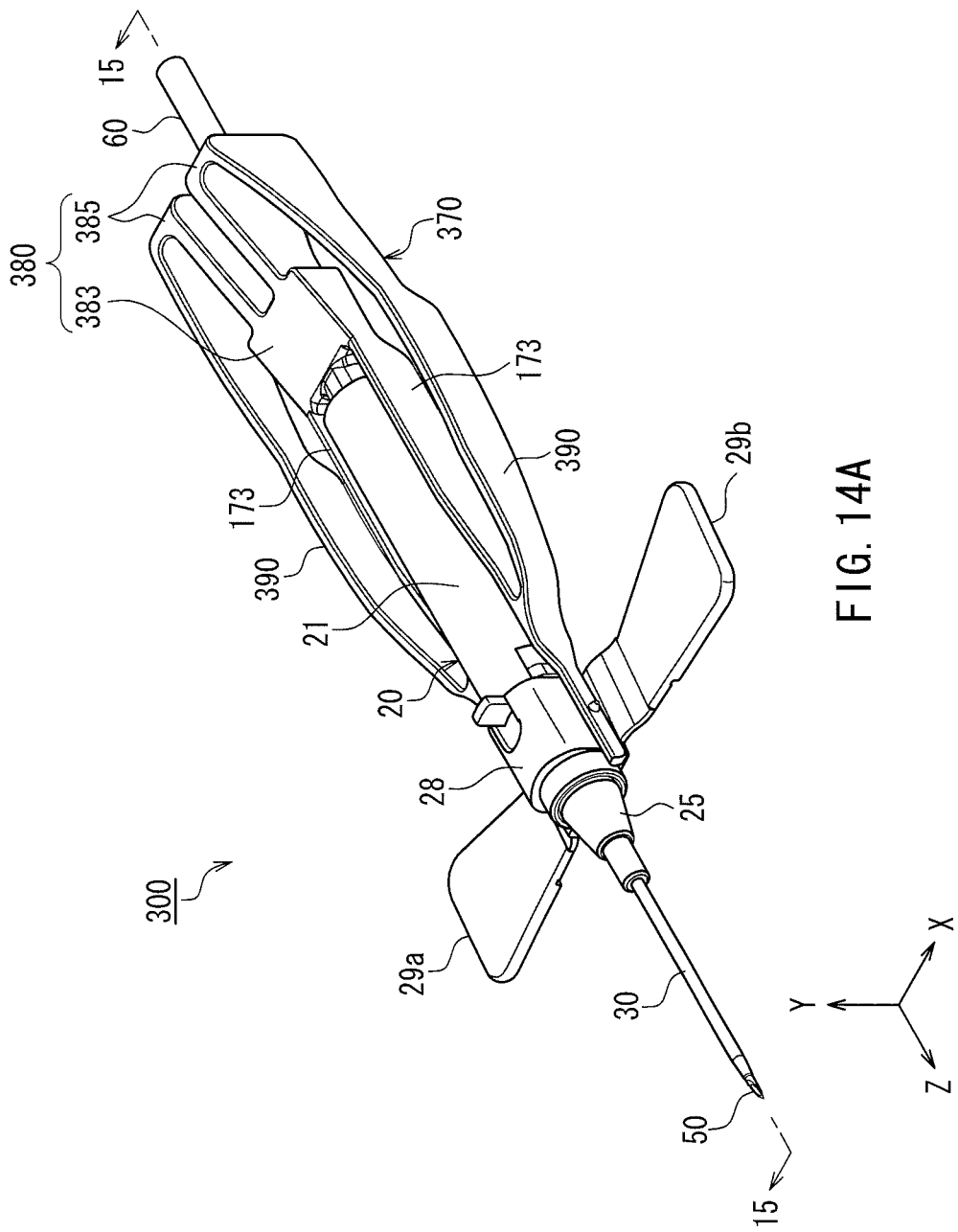
FIG. 14A is a perspective view of an indwelling needle device according to Embodiment 3 of the present invention as seen from above.
Figure 15:
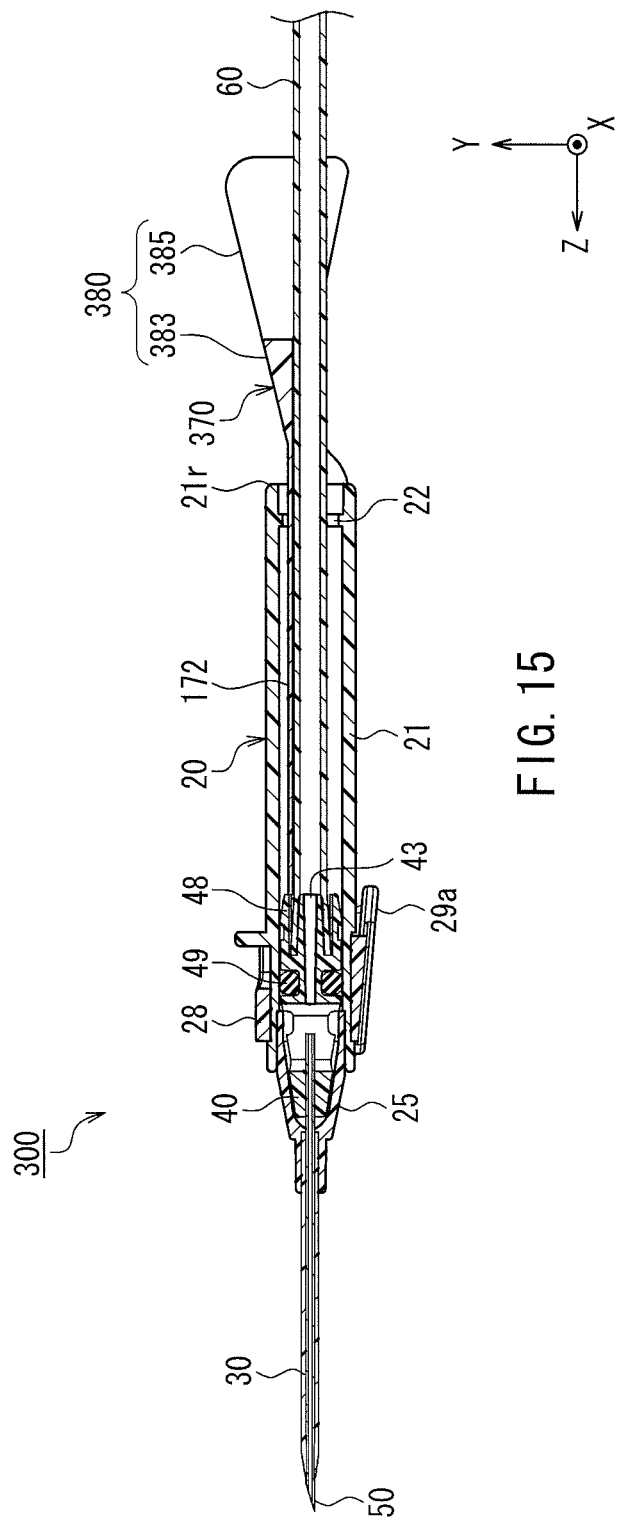
FIG. 15 is a cross-sectional view of the indwelling needle device according to Embodiment 3 of the present invention taken along a vertical plane containing line 15-15 in FIG. 14A and seen in the direction of arrows 15.
Figure 16A:
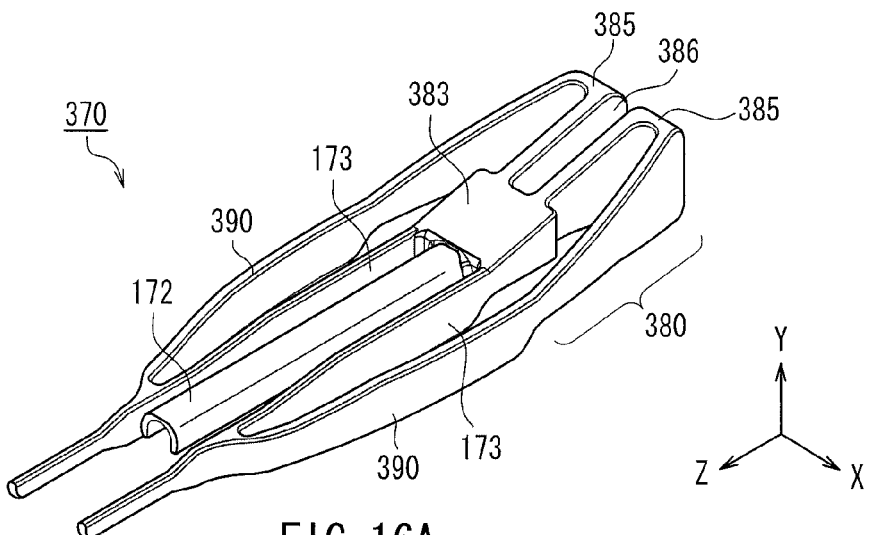
FIG. 16A is a perspective view of a stopper used in the indwelling needle device according to Embodiment 3 of the present invention as seen from above.
Figure 16B:
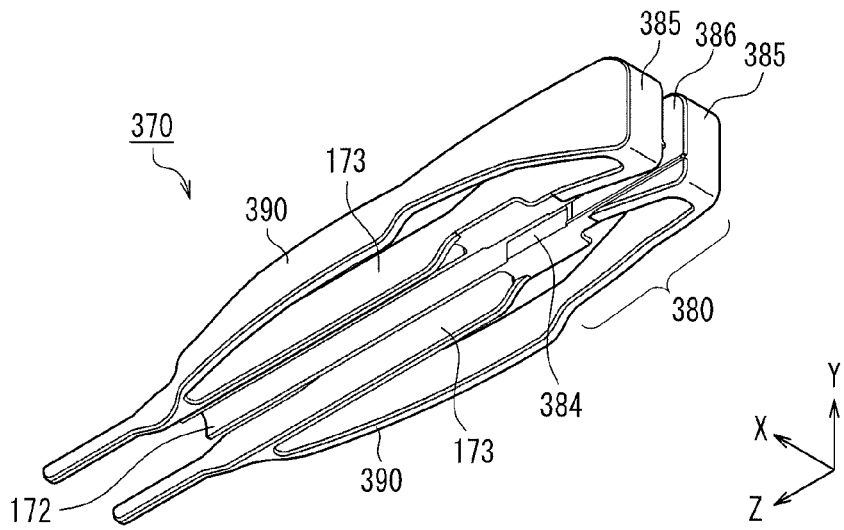
FIG. 16B is a perspective view thereof as seen from below.
Figure 16C:
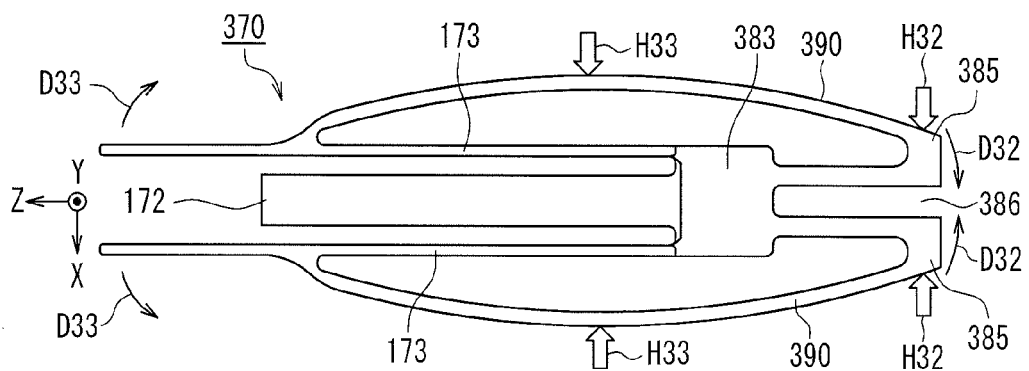
FIG. 16C is a plan view thereof.

FIG. 14A is a perspective view, as seen from above, of the indwelling needle device 300 according to Embodiment 3 of the present invention with the hub 40 being at the initial position, and FIG. 14B is a perspective view thereof as seen from below. FIG. 15 is a cross-sectional view of the indwelling needle device 300 taken along a vertical plane (YZ plane) containing line 15-15 in FIG. 14A and seen in the direction of arrows 15. In Embodiment 3, in order to position and maintain the hub 40 at the initial position, a stopper 370 is used as in Embodiment 1. FIG. 16A is a perspective view of the stopper 370 as seen from above, FIG. 16B is a perspective view thereof as seen from below, and FIG. 16C is a plan view thereof. The stopper 370 of Embodiment 3 includes the insertion portion 172 having an approximately U-shaped cross-section, the pair of plate-like fixing portions 173, a base portion 380, and a pair of bridging portions 390.

The rear portion of the base portion 380 is divided into a pair of grasping portions 385 along a slit 386 that is formed from the rear end of the base portion 380. The pair of grasping portions 385 face each other in the X axis direction, and can be elastically displaced in mutually approaching orientations D32 (see FIG. 16C).

The front portion of the base portion 380 in which the slit 386 is not formed is referred to as a roof portion 383. The upper faces of the roof portion 383 and the grasping portions 385 are inclined so as to be lower toward the insertion portion 172. As shown in FIG. 16B, a groove 384 that connects the insertion portion 172 and the slit 386 in the form of a straight line and that extends in the Z axis direction is formed on the lower side of the roof portion 383.

The insertion portion 172 is disposed between the pair of fixing portions 173, and the insertion portion 172 and the pair of fixing portions 173 extend parallel to the Z axis from the roof portion 383 toward the front side.

As shown in FIG. 16C, the bridging portions 390 link the rear ends of the grasping portions 385 and positions in the vicinity of the front ends of the fixing portions 173. The bridging portions 390 are arranged on sides that are opposite from the insertion portion 172 with respect to the fixing portions 173, and extend away from the roof portion 383 in the X axis direction so as to bulge outward in the X axis direction in the form of arches. In this example, the bridging portions 390 are connected to the rear ends of the grasping portions 385, but they may be connected to positions in the vicinity of the rear ends of the grasping portions 385.

When the rear end portions of the pair of grasping portions 385 (or the rear end portions of the pair of bridging portions 390 or positions in the vicinity thereof) are pushed in the horizontal direction as indicated by arrows H32 in FIG. 16C, the pair of grasping portions 385 are elastically displaced in the mutually approaching orientations D32. Since the bridging portions 390 link the grasping portions 385 and the fixing portions 173, when the pair of grasping portions 385 are displaced in the mutually approaching orientations D32, the front ends of the pair of fixing portions 173 are elastically displaced in the mutually separating orientations D33.

Furthermore, when the middle portions in the Z axis direction of the pair of bridging portions 390 or positions in the vicinity thereof are pushed in the horizontal direction as indicated by arrows H33 in FIG. 16C, this pressure is transmitted via the bridging portions 390 to the grasping portions 385, and the pair of grasping portions 385 are elastically displaced in the mutually approaching orientations D32. At the same time, since the bridging portions 390 link the grasping portions 385 and the fixing portions 173, the front ends of the pair of fixing portions 173 are elastically displaced in the mutually separating orientations D33 as described above.

As shown in FIGS. 14A, 14B, and 15, the insertion portion 172 of the stopper 370 is inserted into the inner cavity of the shield tube 21 from the rear end of the shield tube 21. As in Embodiment 1, when the leading end of the insertion portion 172 pushes the hub 40 toward the front side, the hub 40 can be disposed at the initial position within the inner cavity of the shield 20. The tube 60 connected to the hub 40 is fitted to the insertion portion 172 having an approximately U-shaped cross-section, the groove 384 on the lower side of the roof portion 383, and the slit 386 between the grasping portions 385. The base portion 380 is located outside the shield tube 21.

Although not shown, the cross-sectional shape along the XY plane of the roof portion 383 is substantially the same as the cross-sectional shape along the XY plane of the roof portion 183 of Embodiment 1 (see FIG. 5). The inner circumferential face of the groove 384 of the roof portion 383 has an approximately U-shaped cross-section, and the tube 60 is fitted to the groove 384. Part of the outer circumferential face of the tube 60 facing downward is exposed, and the remainder thereof is covered by the roof portion 383. As in Embodiment 1, it is preferable that part of the exposed lower outer circumferential face of the tube 60 slightly protrudes downward from the lower face of the roof portion 383.

The operational methods of the thus configured indwelling needle device 300 of Embodiment 3 are substantially the same as those of the indwelling needle device 100 of Embodiment 1.

Figure 17A:
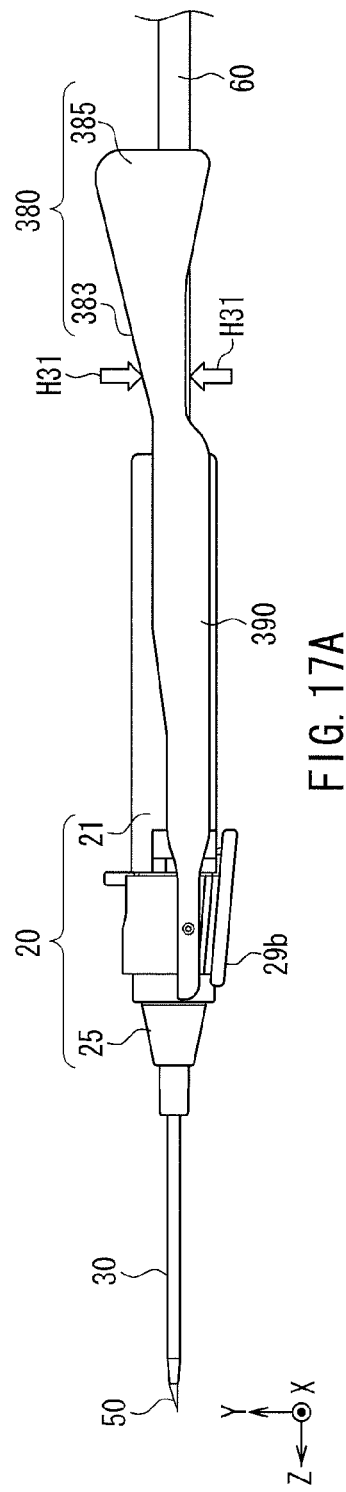
Figure 17B:
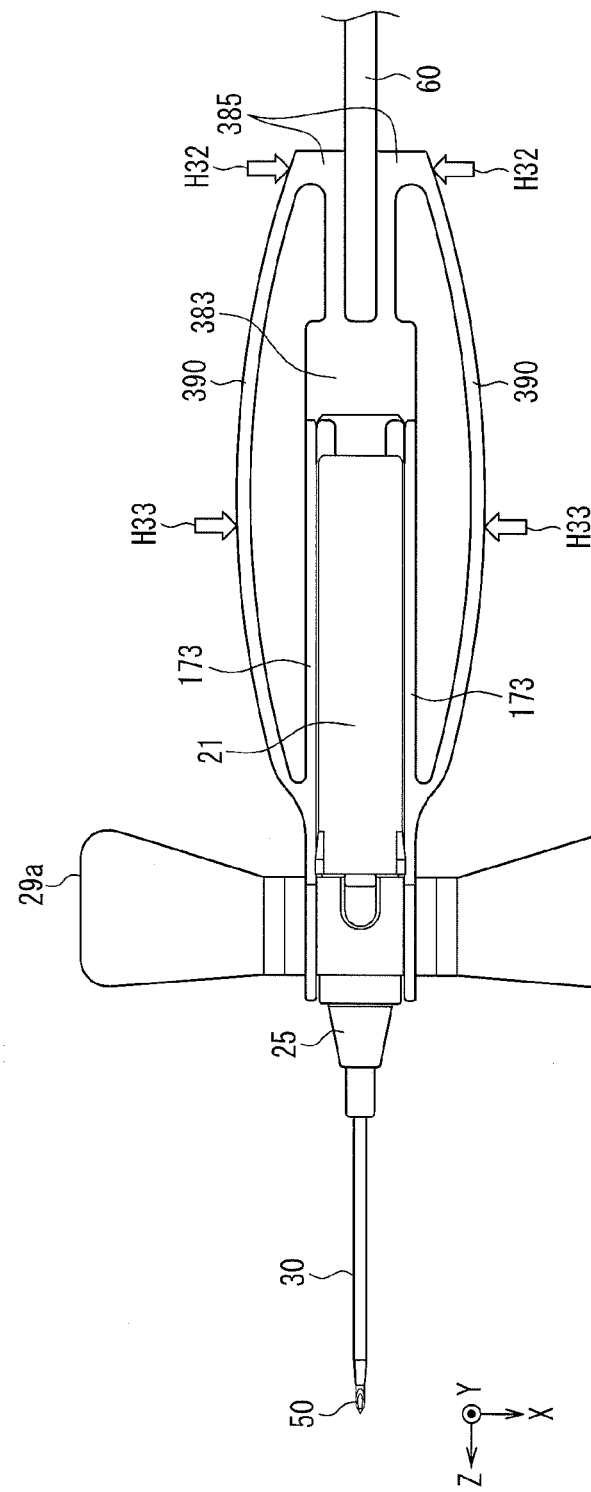

That is to say, the inner needle 50 and the outer needle 30 are inserted into a blood vessel of the patient in a state in which the hub 40 is maintained at the initial position (see FIGS. 14A, 14B, and 15). The methods for gripping the indwelling needle device 300 at this time may be substantially the same as the first to fourth gripping methods described in Embodiment 1. FIGS. 17A and 17B show typical grip positions of the indwelling needle device 300. In the first gripping method, the roof portion 383 of the stopper 370 is gripped with two fingers in the vertical direction (Y axis direction) as indicated by arrows H31 in FIG. 17A. In the second gripping method, the rear end portions of the pair of grasping portions 385 (or the rear end portions of the pair of bridging portions 390 or positions in the vicinity thereof) of the stopper 370 are gripped with two fingers in the horizontal direction (X axis direction) as indicated by arrows H32 in FIG. 17B. In the third gripping method, the middle portions in the Z axis direction of the pair of bridging portions 390 of the stopper 370 or positions in the vicinity thereof are gripped with two fingers in the horizontal direction (X axis direction) as indicated by arrows H33 in FIG. 17B. In the fourth gripping method, the wings 29a and 29b are bent upward so as to overlap each other, and are gripped with two fingers in the horizontal direction (X axis direction) (not shown).

After the inner needle 50 and the outer needle 30 are inserted into a blood vessel of the patient, the hub 40 is moved to the retracted position (see FIGS. 7 and 8). Thus, it is necessary to pull the stopper 370 out of the shield 20, and to pull the tube 60 from the shield 20. As in Embodiment 1, the operator can pull the stopper 370 out of the shield 20 while gripping the base portion 380.

For example, the roof portion 383 of the base portion 380 can be gripped in the vertical direction (Y axis direction) as in the first gripping method (arrows H31 in FIG. 17A). As shown in FIG. 14B, the outer circumferential face of the tube 60 is partially exposed on the lower side of the roof portion 383, and, thus, the roof portion 383 and the tube 60 can be gripped together. Accordingly, when the stopper 370 is pulled from the shield 20, the tube 60 can be pulled together with the stopper 370.

Alternatively, the rear end portions of the pair of grasping portions 385 of the base portion 380 (or the rear end portions of the pair of bridging portions 390 or positions in the vicinity thereof) can be gripped in the horizontal direction (X axis direction) as in the second gripping method (arrows H32 in FIG. 17B). In this case, the pair of grasping portions 385 are elastically displaced in the orientations indicated by arrows D32 (see FIG. 16C) and grasp the tube 60 located therebetween. Accordingly, when the stopper 370 is pulled from the shield 20, the tube 60 can be pulled together with the stopper 370.

Moreover, in Embodiment 3, the middle portions in the Z axis direction of the pair of bridging portions 390 or positions in the vicinity thereof can be gripped in the horizontal direction (X axis direction) as in the third gripping method (arrows H33 in FIG. 17B). Also in this case, the pair of grasping portions 385 are elastically displaced in the orientations indicated by arrows D32 (see FIG. 16C) and grasp the tube 60 located therebetween. Accordingly, when the stopper 370 is pulled from the shield 20, the tube 60 can be pulled together with the stopper 370.

As described above, when the base portion 380 is gripped in the vertical direction or in the horizontal direction or the pair of bridging portions 390 are gripped in the horizontal direction, and the stopper 370 is withdrawn from the shield 20, the tube 60 can be pulled together with the stopper 370. Accordingly, the possibility can be reduced of an operational error occurring in which the operator pulls out only the stopper 370 after the puncture and forgets to house the inner needle 50 within the shield 20.

Furthermore, when puncture with the inner needle 50 and the outer needle 30 has been performed in a state in which the base portion 380 is gripped in the vertical direction (the first gripping method, see arrows H31 in FIG. 17A) or in the horizontal direction (the second gripping method, see arrows H32 in FIG. 17B) and when puncture with the inner needle 50 and the outer needle 30 has been performed in a state in which the pair of bridging portions 390 are gripped in the horizontal direction (the third gripping method, see arrows H33 in FIG. 17B), the inner needle 50 can be housed within the shield 20 after the puncture, without changing the grip position. Accordingly, a series of operations can be performed quickly and efficiently.

With the stopper 370 of Embodiment 3, as described with reference to FIG. 16C, the elastic displacement of the pair of grasping portions 385 in the orientations D32 can cause the pair of fixing portions 173 to be displaced in the orientations D33. Accordingly, in the case of applying the second gripping method (see arrows H22 in FIG. 13B) or the third gripping method (see arrows H33 in FIG. 17B), interference can be avoided between the fixing portions 173 and the shield 20 when inserting the insertion portion 172 into the shield 20 and when pulling the stopper 370 out of the shield 20.

As can be seen from the description above, the stopper 370 of Embodiment 3 includes the pair of bridging portions 390. Thus, using any one of the first to third gripping methods, the inner needle 50 can be housed within the shield 20 simultaneously with pulling the stopper 370 out of the shield 20. Although the number of types of gripping method that can perform puncture and then house the inner needle 50 without changing the grip position is two in Embodiments 1 and 2, the number has been increased to three in Embodiment 3.

In the foregoing example, the bridging portions 390 bulge outward in the form of arches, but the shape of the bridging portions 390 is not limited to this. As long as at least the pair of grasping portions 385 can be elastically displaced in the orientations D32 by gripping the pair of bridging portions 390 as described above, the bridging portions 390 may have any shape such as straight lines, triangles, or trapezoids.

In the foregoing example, when the pair of bridging portions 390 are displaced so as to approach each other in the orientations indicated by arrows H33 (see FIG. 16C), the front ends of the pair of fixing portions 173 are displaced in the mutually separating orientations D33, but the present invention is not limited to this. For example, designs may be employed in which, when the pair of bridging portions 390 are displaced, the pair of fixing portions 173 are hardly displaced, or the pair of fixing portions 173 are displaced in mutually approaching orientations.

Embodiment 3 is same as Embodiment 1 except for the aspects described above. The various modified example described in Embodiment 1 can be applied also to Embodiment 3.

Embodiments 1 to 3 should be considered as illustrative only. The present invention is not limited to Embodiments 1 to 3, and appropriate changes can be made thereto.

The configuration of the stopper is not limited to those described in the foregoing embodiments. For example, the pair of fixing portions 173 may be omitted in the stoppers 170 and 270 described in Embodiments 1 and 2.

Although the stoppers 170, 270, and 370 described in the foregoing embodiments are left-right symmetrical when seen from above, the present invention is not limited to this, and the stoppers also may be left-right asymmetrical.

The pair of grasping portions may be arranged between the insertion portion and the roof portion. Furthermore, the base portion of the stopper may have portions other than the roof portion and the grasping portions.

The fitting structure for fitting the hub 40 located at the retracted position and the shield 20 to each other may also have a configuration other than the above-described configuration. Alternatively, the fitting structure may be omitted.

INDUSTRIAL APPLICABILITY

There is no particular limitation on the field of use of the present invention, and the present invention can be extensively used as an indwelling needle device for use in such treatments as infusion, blood transfusion, extracorporeal blood circulation, and the like. Among these, the present invention can be preferably used as an indwelling needle device for hemodialysis.

LIST OF REFERENCE NUMERALS 100, 200, 300 Indwelling needle device
20 Shield
21 Shield tube
25 Outer hub
30 Outer needle
40 Hub
50 Inner needle
60 Tube
170, 270, 370 Stopper
172 Insertion portion
173 Fixing portion
180, 280, 380 Base portion
183, 283, 383 Roof portion
184, 284, 384 Groove
185, 285, 385 Grasping portion
186, 286, 386 Slit
390 Bridging portion

The invention claimed is:

1. An indwelling needle device, comprising:
a shield that has an inner cavity;
a soft outer needle that is fixed to a front end of the shield;
a hub that is disposed within the inner cavity of the shield and is movable in a longitudinal direction of the shield;
a hard inner needle that is fixed to a front end of the hub;
a tube that is connected to a rear end of the hub; and
a stopper that can be inserted into and pulled out of the inner cavity of the shield from a rear end of the shield;
wherein the hub can be displaced between an initial position at which the hub is located on a front end side of the inner cavity of the shield and the inner needle penetrates the outer needle and protrudes from a leading end of the outer needle and a retracted position at which the hub is located on a rear end side of the inner cavity of the shield and the inner needle is housed within the inner cavity of the shield,
the stopper includes an insertion portion that is inserted into the inner cavity of the shield and a base portion that is located on a rear end of the insertion portion,
when the insertion portion is inserted into the inner cavity of the shield and a leading end thereof is caused to abut against the hub located at the initial position, the base portion is located outside the shield,
the base portion includes a roof portion that exposes part of an outer circumferential face of the tube and covers a remainder thereof, and a pair of grasping portions that are arranged to sandwich the tube and can be elastically displaced so as to grip the tube, and
a groove to which the tube is fitted is formed in a lower face of the roof portion, and a width of the groove is smaller than an outer diameter of the tube so that the tube is elastically compressed and deformed,
wherein the part of the outer circumferential face of the tube that is exposed protrudes downward from the lower face of the roof portion.

2. The indwelling needle device according to claim 1, wherein a dimension of the pair of grasping portions in a direction orthogonal to a direction in which the pair of grasping portions sandwich the tube and to a longitudinal direction of the insertion portion is larger than that of the roof portion.

3. The indwelling needle device according to claim 1, wherein the roof portion and the pair of grasping portions are arranged in that order from an insertion portion side.

4. The indwelling needle device according to claim 3, wherein an upper face of the roof portion is inclined such that a height in a direction orthogonal to a direction in which the pair of grasping portions sandwich the tube and to a longitudinal direction of the insertion portion is lower toward the insertion portion.

5. The indwelling needle device according to claim 1, wherein the roof portion causes part of the outer circumferential face of the tube to be exposed in a direction orthogonal to a direction in which the pair of grasping portions sandwich the tube and to a longitudinal direction of the insertion portion.

6. The indwelling needle device according to claim 1,
wherein the stopper further includes a pair of fixing portions that are arranged to sandwich the insertion portion, and when the pair of grasping portions are elastically displaced so as to grip the tube, the pair of fixing portions are displaced in orientations in which the fixing portions move away from the insertion portion.

7. The indwelling needle device according to claim 1,
wherein the pair of grasping portions are positioned on sides that are opposite from the insertion portion with respect to the roof portion, the stopper further includes a pair of fixing portions that are disposed to sandwich the insertion portion and a pair of bridging portions, the pair of bridging portions sandwich the roof portion in a first direction parallel to the direction in which the pair of grasping portions sandwich the tube; the pair of bridging portions being spaced away from the roof portion in the first direction, and when the pair of bridging portions are elastically displaced so as to approach each other, the pair of grasping portions are displaced so as to grip the tube.

8. The indwelling needle device according to claim 1,
wherein the groove has a pair of side faces, and the pair of side faces are disposed to face each other and are generally parallel to each other.

* * * * *